(12) United States Patent
Legrand et al.

(10) Patent No.: US 8,334,254 B2
(45) Date of Patent: *Dec. 18, 2012

(54) RECOMBINANT LACTOFERRINS, METHODS OF PRODUCTION FROM PLANTS AND USES THEREOF

(75) Inventors: Dominique Legrand, Villeneuve d'Ascq (FR); Valerie Salmon, Montville (FR); Genevieve Spik, Marcq en Barouel (FR); Veronique Gruber, Chamalieres (FR); Philippe Bournat, Clermont-Ferrand (FR); Bertrand Merot, Volvic (FR)

(73) Assignee: EDULIS, Lyon (FR)

( * ) Notice: Subject to any disclaimer, the term of this patent is extended or adjusted under 35 U.S.C. 154(b) by 868 days.

This patent is subject to a terminal disclaimer.

(21) Appl. No.: 12/099,462

(22) Filed: Apr. 8, 2008

(65) Prior Publication Data

US 2011/0092411 A1    Apr. 21, 2011

Related U.S. Application Data

(60) Continuation of application No. 10/446,234, filed on May 27, 2003, now Pat. No. 7,354,902, which is a division of application No. 09/423,097, filed as application No. PCT/FR98/00895 on May 4, 1998, now Pat. No. 6,569,831.

(30) Foreign Application Priority Data

May 2, 1997 (FR) .................................. 97 05699

(51) Int. Cl.
*C07K 14/79* (2006.01)
*C12N 15/12* (2006.01)
(52) U.S. Cl. ......... 514/2.5; 514/1.1; 530/350; 435/69.1; 435/320.1; 435/252.3; 435/410; 800/288
(58) Field of Classification Search ............... 514/12, 514/8, 1.1, 2.5; 530/350; 536/23.1; 435/69.1, 435/320.1, 252.3, 410; 800/288
See application file for complete search history.

(56) References Cited

U.S. PATENT DOCUMENTS 7,354,902 B2 * 4/2008 Legrand et al. ................ 514/2.5

FOREIGN PATENT DOCUMENTS

WO     WO 96/37094     * 11/1996

OTHER PUBLICATIONS

Ward et al., Biotechnology 13, 498-503 (May 1995).*

* cited by examiner

*Primary Examiner* — Chih-Min Kam
(74) *Attorney, Agent, or Firm* — B. Aaron Schulman, Esq.; Stites & Harbison PLLC

(57) ABSTRACT

The invention concerns the use of a recombinant nucleotide sequence containing a cDNA coding for a lactoferrin, in particular human lactoferrin, or the derived proteins, and elements enabling a plant cell to produce lactoferrin or the derived proteins, coded by the cDNA, in particular a transcription promoter and terminator identified by the plant cell transcription machinery, to transform plant cells in order to obtain, from these cells, or plants obtained therefrom, lactoferrin or derived proteins.

20 Claims, 7 Drawing Sheets

MM(kDa)    1    2

RECOMBINANT LACTOFERRINS, METHODS OF PRODUCTION FROM PLANTS AND USES THEREOF

CROSS-REFERENCE TO RELATED APPLICATIONS

This application is a continuation of U.S. application Ser. No. 10/446,234, filed May 27, 2003, now issued as U.S. Pat. No. 7,354,902, which was a divisional of U.S. application Ser. No. 09/423,097, having a filing date of Mar. 21, 2000, now issued as U.S. Pat. No. 6,569,831, which is the National Stage of International Application No. PCT/FR98/00895, filed May 4, 1998.

The present invention relates to recombinant lactoferrins (rLf), their production from plants, and uses thereof.

The use of certain proteins found in mammals has been questioned due to the possibility of contamination by non conventional infectious agents, particularly of the prion type. The impact on marketing and regulations is great. The development of proteins free of all animal contamination is, therefore, a new possibility but one which faces new difficulties depending on the protein and the plant matter chosen.

Prior art includes the publication by Mitra et al. (1994), which describes the transformation of tobacco cells with the DNA sequence which codes for human lactoferrin. However, this publication is limited to plant cells, and does not allow for the production of regenerated plants from these cells. Furthermore, the protein expressed is not purified, and seems, in any case, imperfect as only a part (48 kDa) is detected, and not the entire protein.

In the prior art, application WO 9637094 is also known; this describes the production of plants which are resistant to viruses, by means of transforming them with a gene which codes for lactoferrin. However, in this document as well, the protein is not purified and the only indication of its presence is a Weston blot test.

As a result of the complexity of lactoferrin and the characteristics of the plant matter used, the extraction and purification procedures also represent major obstacles in the production of lactoferrin from plants. The difficulties posed by these two procedures can represent a new set of problems for each protein which one wishes to produce from a plant.

Lactoferrin is a glycoprotein of the transferrin family. Following its discovery in human milk, lactoferrin was shown to be present in many other species such as cows, goats, pigs, mice and guinea pigs, but a highly variable concentrations. In human milk, the concentration of lactoferrin is in the range of 1 to 2 g/l; the concentration is particularly high in colostrum and diminishes over the course of lactation. In milk, lactoferrin is present primarily in the apo form, that is to say, unsaturated in iron. Lactoferrin has also been found in many other secretions, such as the saliva, bile, pancreatic fluid, and secretions of the small intestine. It is found in most mucus, such as bronchial, vaginal, nasal and intestinal secretions.

Lactoferrin is also present in polymorphonuclear neutrophilic leucocytes, where it is localized in the secondary granules of cells that do not contain myeloperoxidase. Leucocytic lactoferrin is synthesized during granulopoiesis of the promyelocyte stage of the metamyelocyte stage. When the neutrophils degranulate, lactoferrin is released into the plasma at a relatively low concentration (0.4 to 2 mg/l) as compared with the level of transferrin found in the blood (2 to 3 g/l).

The peptide sequence for human lactoferrin (hLf) was determined in 1984 by Metz-Boutigue et al. This sequence of 692 amino acids was confirmed by way of cloning of the cDNA for lactoferrin of the human mammary gland (Powell and Ogden, 1990, Rey et al., 1990). Lactoferrin and serotransferrin have very similar primary structures and spatial configurations. Their polypeptide chains are formed of two lobes (N terminal lobe and C terminal lobe) joined by a small alpha helix peptide. Sequence similarities between the N and C terminal halves of human lactoferrin reach 37%. Tryptic hydrolysis of human lactoferrin allowed Legrand et al. (1984) to produce the 30 kDa N trypsic (N-t) fragment (residues of amino acids 4 to 283), and the 50 kDa C trypsic (C-t) fragment (residues of amino acids 284 to 692). At equimolar proportions, these fragments can reunite to form a non-covalent N-t/C-t complex which has electrophoretic and spectroscopic characteristics similar to those of human lactoferrin (Legrand et al, 1986).

Lactoferrin can reversibly bind two ferric ions which results in a salmon-pink coloration, the maximum absorption of which is centered at 465 nm. The binding of each ferric ion requires the same of a carbonate ion. At a pH of 6.4, the association constant of the complex [Fe3+]2-Lf is in the range of $10^{24}$ $M^{-1}$, which decreases with pH. X-ray diffraction study of human lactoferrin at 3.2 Å to 2.8 Å and at 2.2 Å show that each ferrous ion is coordinated with 2 tyrosine residues, a histidine, an aspartic acid and a carbonate ion. These amino acids are the same in both lobes. Both lactoferrin iron binding sites have a strong affinity for this metal, but they release it at different pH levels. The N-t lobe releases its iron at pH 5.8 (acid labile lobe), while the C-t lobe (acid stable lobe) releases its iron at pH 4. Other ions may bind to the protein, in particular gallium. Researchers interested in the use of a $^{67}$Ga-Lf complex as a tracer in cancer diagnostics have shown that following injection with $^{67}$Ga, the complex is preferentially found in the mammary tissues, in physiological and pathological secretions and in Burkitt and Hodgkin lymphomas.

In terms of glycosylation, lactoferrin isolated from human milk has three glycosylation sites, $Asn^{138}$, $ASN^{479}$ AND $Asn^{624}$, the first located on the N-t lobe and the other two on the C-t lobe. Glycosylation occurs preferentially at two sites ($Asn^{138}$ and $ASN^{479}$) in 85% of molecules, while glycosylation of one site ($Asn^{479}$) and of the three sites simultaneously happens in 5% and 9% of cases, respectively. Lactoferrin glycans are of the mono or disialylated and fucosylated N-acetyllactosamine type (Spik et al, 1982). The fucose residues are α (1,6) branched on the N-acetylglucosamine 5' of the attachment point, or are α (1,3) branched on the N-acetylglucosamine 5' of the antenna. Leucocytic lactoferrin differs from that above by the total absence of fucose.

While serotransferrin is unquestionably the principal transporter of iron in all the cells of the organism, the roles played by lactoferrin appear to be essentially linked to defense of the organism and inflammatory mechanisms, working either directly on pathogenic micro-organisms, or indirectly on the effector immune cells.

Lactoferrin is an anti-microbial agent which works by way of several mechanisms. The first of these is the bacteriostatic effect of lactoferrin by means of iron deprivation (Spik et al., 1978). By taking up iron from its surroundings, lactoferrin inhibits bacteria division, as iron is an indispensable element in the biosynthesis of DNA. Furthermore, a more complex mechanism which causes antibodies to act has been shown. The bacteriostatic activity of lactoferrin increases in the presence of the specific IgA and IgG of the pathogenic bacterium. At the same time, lysozyme can associate its lytic activity on the walls of Gram+ bacteria with the action of lactoferrin. Thus, in milk, lactoferrin, lysozyme and antibodies can act synergistically in case of microbe attack.

The second anti-bacterial effect of lactoferrin is linked to it bactericidal capacity. Lactoferrin appears to bind to the walls of Gram– bacteria, which appears to destabilize them and to provoke the release of lipopolysaccharides (LPS). Thus it would seem that the walls become more fragile and more susceptible to the effects of hydrophobic antibiotics. These theories have been confirmed by use of electron microscopy which shows the destabilizing effects of lactoferrin on Gram– bacteria, including *E. coli*. A hypothesis has been made to the effect that the binding of lactoferrin occurs on the A lipid of the LPS, and that this is followed by the extraction of these LPS from the external membranes of the bacteria, irreparably damaging them. The bactericide regions of human lactoferrin (lactoferrin A) and bovine lactoferrin (lactoferrin B) have recently been identified. They are both found in an N-terminal lobe loop comprising 18 amino acids. This loop is formed by a disulphur bridge between the residues Cys 30 and 37 for human lactoferrin, and 19 and 36 for bovine lactoferrin. In addition, the importance of the loop formed by residues 28-34 of human lactoferrin in its binding to LPS has been demonstrated.

Thus, due to its bacteriostatic and bactericide activities, lactoferrin present in human milk protects nursing infants from infantile diarrheas.

An anti-fungal effect has been established for lactoferrin with respect to several strains of *Candida*. Studies have also been carried out with bovine lactoferrin showing this action both on yeasts and on filamentous fungi. Also, the effect of bovine lactoferricin appears to be greater than that of whole bovine apolactoferrin and similar to that of polymyxin B, an antibiotic of the cationic peptide type, known for its membrane destabilisation properties. It has also been shown that lactoferrin B interacts directly with the surface of the fungus, thereby introducing changes to its ultrastructure.

Recently, an antiviral activity has been demonstrated for lactoferrin by several authors. Certain types of virus penetrate the cells by means of a mechanism which causes absorption of proteoglycans by the membranes of the target cells, followed by binding at a specific receptor and fusion of the viral membrane with that of the host. As it is highly basic, lactoferrin binds to the heparan sulphates of cells, and is thereby able to inhibit the adsorption of several types of virus. Highly conclusive in vitro studies have been carried out using HIV (human immunodeficiency virus) and HCMV (human cytomegalovirus) with a CI50 in the range of 10 µg/ml. Similar results have been achieved with HSV-1 (herpes simplex virus type 1). This work showed not only blocking of virus receptors (heparan sulphates, proteoglycans, LDL receptor), but also a possible interaction between lactoferrin and the virus. These recently discovered roles represent new possibilities for prevention and treatment, particularly in terms of immunodeficiency illnesses or recurrent illnesses, in terms of these viral infections.

One of the consequences of tissue inflammation is the formation of free radicals and the peroxidation of lipids. The formation of these free radicals results particularly from the phagocytosis mechanisms of the micro-organisms. According to the Haber-Weiss reaction, free radicals are created as the result of ferric iron, which acts as a reaction catalyst. It has been shown in vivo that lactoferrin, coming from the degranulation of neutrophils, stops the formation of extra-cellular free radicals by immediately taking up the iron which would catalyse the formation of these radicals. As the result of this action, lactoferrin prevents tissues from being damaged. By means of a similar mechanism, lactoferrin inhibits the peroxidation of lipids and thus protects the cellular membranes to which it binds. These studies also showed that lactoferrin has anti-oxidising and anti-inflammatory effects if the protein is in the form without iron.

Lactoferrin released by leucocyte granules has been identified as an inhibitor of granulocyte and macrophage colonies by reducing the production of GM-CSF (granulocyte and macrophage colony stimulation factor). The mechanism involved seems complex, as lactoferrin appears to act by inhibiting the release of a monokine, which is itself responsible for the release of GM-CSF by the lymphocytes, the fibroblasts and the endothelial cells. This monokine has been identified at IL1.

Many of the roles played by lactoferrin, such as the suppression of the production of antibodies, regulation of complement activation and regulation of NK (natural killer) cells activity, suggest mechanisms which are regulated by cytokines. Studies show that lactoferrin can exert a negative retrocontrol on certain cytokines such as the IL1, the IL2 and the TNFa, so as to prevent the activation of leucocytes in inflammation areas.

Zimecki et al (1991) showed that immature CD4– CD8– thymocytes incubated in the presence of lactoferrin acquire the marker CD4+ characteristic of auxiliary lymphocytes. These authors also point out various phenotypic and functional changes in B cells in the presence of lactoferrin (Zimecki et al., 1995). A specific receptor for human lactoferrin has been defined for activated lymphocytes (Mazurier et al., 1989). In addition, the site of interaction between lactoferrin and its lymphocytic receptor has been described: Legrand et al. (1992) showed that it was contained in the N terminal region, and more specifically, in the first 50 residues of lactoferrin.

Lactoferrin appears to regulate the cytotoxic activity of NK (natural killer) cells and LAK cells at very low quantities (0.75 µg/ml). Lactoferrin significantly increases the cytotoxic activity of NK cells with respect to tumour cells and cells infected by retroviruses. Lactoferrin also effects, the cytotoxicity of monocytes. The cause of this stimulation by lactoferrin of the cytotoxic activity of NK cells, of lymphocytes and also adherent cells may be the result of either activation of the killer cells following the internalisation of lactoferrin, or of a modification of the target cells which then become more susceptible to lysis.

Lactoferrin also seems to play a immunoregulatory role in inflammatory responses (Elass-Rochard et al., 1995; confirmed by Elass-Rochard et al., 1998). Demonstration of anti-tumour activity was also the object of studies by Salmon et al. (1998).

Lactoferrin has a growth factor effect on various cells in environments lacking in foetal veal serum. This activity has been demonstrated, particularly on the B and T lymphocytic strain with respect to a macrophage murine strain (P388 DI). Lactoferrin also stimulates the incorporation of thymidine tritiate in the DNA of rat enterocytic cells.

The role of iron in growth factor activity is still an object of controversy. According to some authors, lactoferrin works by providing the iron necessary to cellular proliferation. Others hold that iron is not involved, and that the mitogen activity is due solely to the protein itself.

The hypothesis to the effect that lactoferrin is involved in the intestinal absorption of iron results from the observation that amongst breast-fed infants, the incidence of iron deficiency is very low. In fact, only such children maintain a major supply of iron up to the age of 6 months, which implies high bioavailability for iron contained in human milk. The percentage of absorption can reach 81% during the first three months of life, and diminishes rapidly thereafter. Amongst the various components of human milk, lactoferrin is the best candidate for explanation of both the great bioavailability of iron in milk and regulation of its absorption. Cox et al. studied the importance of lactoferrin in the absorption of iron by the human intestine as early as 1979. The enterocytic receptor for lactoferrin was first shown to be present in rabbits, then in mice. Finally, the human enterocytic receptor was studied. It was shown that, with HT29 enterocytic cell cultures, the number of lactoferrin receptors doubled in the presence of iron chelator (Mikogami et al., 1994, 1995). This increase is due to a de novo synthesis of receptors. The expression of the lactoferrin receptor is, therefore, regulated by a lack of iron, and this lack also induces an increase in the internalisation of the lactoferrin receptor by the enterocytes. Thus, lactoferrin seems to be involved in iron nutrition, in particular, in case of iron deficiencies.

Not only has the cDNA sequence for human lactoferrin been determined, but the cDNA sequence for various animal species has been established. Specifically, sequences have been found for:
  bovine lactoferrin (Pierce et al., 1991)
  porcine lactoferrin (Alexander B. F. et al., 1992)
  murine lactoferrin (Shirsat N. V. et al., Gene, 1992)
  caprine lactoferrin (Le Provost F. et al., 1994).

Analysis of peptide sequences corresponding to cDNA sequences indicates major similarities. In particular, the human lactoferrin sequence shows a 69% correspondence with that of cows. As with human lactoferrin, the nucleotide sequence of bovine lactoferrin cDNA contains a signal peptide composed of 16 amino acids.

This structural similarity results in functional similarities. In particular, as the N-terminal end of both bovine and human lactoferrin have a great number of basic amino acids, these two lactoferrins are recognised in a similar way by many constituent acids. It should be noted, for example, that these two proteins have similar interactions with the lipopolysaccharides of Gram-bacteria and the proteoglycans which are found on the surface of many cells. (Elass-Rochard E., et al., 1995).

These interactions appear to imply that these two lactoferrins may play the same role in the inhibition of release of cytokines of macrophages activated by lipopolysaccharides, and therefore in inflammatory reaction mechanisms.

In the same manner, these two lactoferrins show the same binding characteristics for enterocytic cells and, therefore, play the same role in intestinal iron absorption and various anti-bacterial and anti-viral activities.

Thus, the many roles played by lactoferrin, and especially its antioxidant, anti-microbial and anti-viral activities make this protein of major importance in terms of treatment, and above all prevention, of bacterial, fungal and viral infections, and also in terms of the prevention of septic shock which, classically, occurs after surgical operations.

The immunoregulatory and anti-tumour activities of lactoferrin can also be used in the treatment of inflammation and cancer (Denis et al.; Zimecki et al.).

Lactoferrin can also be used in dermo-pharmaceutical and cosmetic treatments, for example in a cosmetic anti-free-radical treatment, or to protect hair keratin against atmospheric damage.

DETAILED DESCRIPTION OF THE INVENTION

The invention concerns:
the use of a recombinant nucleotide sequence containing both: a cDNA coding for a lactoferrin, particularly for mammalian lactoferrin, preferably bovine, porcine, caprine or human lactoferrin, or derived proteins (derived protein meaning any protein having at least 70% correspondence with the target protein, particularly at least 80%, for example between 85 and 100% correspondence and/or having a different glycosylation profile wile maintaining the functional characteristics of the reference lactoferrin); and the elements required by a plant cell to produce the lactoferrin or derived proteins coded by said cDNA, particularly a transcription promoter and terminator recognised by the transcriptional machinery of plant cells, so as to produce from these cells, or from plants produced therefrom, lactoferrin or derived proteins.

a recombinant nucleotide sequence characterised in that it contains both: a sequence coding for lactoferrin, particularly for mammalian lactoferrin, preferably bovine, porcine, caprine or, human lactoferrin, or derived proteins; and the elements required by a plant cell to produce the lactoferrin or derived proteins coded by said cDNA, particularly a transcription promoter and terminator recognised by the transcriptional machinery of plant cells. Advantageously, the nucleotide sequence contains a sequence coding for a signal peptide responsible for the secretion of recombinant polypeptides.

a vector, particularly a plasmid, containing a nucleotide sequence according to the invention inserted, as necessary, at a site which is not essential for its replication.

a cellular host, particularly any bacteria such as *Agrobacterium tumefaciens* transformed by a vector according to the invention, a method of producing lactoferrin, particularly human lactoferrin, or derived proteins, characterised in that it comprises:

transformation of plant cells, particularly by means of a cellular host according to the invention, this itself having been transformed by a vector according to the invention, so as to integrate a recombinant sequence according to the invention within the genome of these cells, as necessary, the production of transformed plants from the aforementioned transformed cells, recuperation of recombinant lactoferrin, particularly human lactoferrin, or derived proteins produced in said aforementioned transformed cells or plants, particularly by extraction followed, as necessary, by purification, a genetically transformed plant, plant extract or part of a plant, particularly leaves and/or fruits and/or seeds and/or plant cells, characterised in that it contains one (or several) recombinant nucleotide sequence(s) according to the invention which is (are) integrated in a stable manner in the genome thereof, these plants being particularly chosen from amongst rape, tobacco, maize, peas, tomatoes, carrots, wheat, barley, potatoes, soy, sunflower, lettuce, rice, alfalfa and beets.

a lactoferrin, particularly a human lactoferrin, or a derived protein, characterised in that it is obtained by means of the method of the invention, a genetically transformed plant, plant extract or part of a plant, particularly leaves and/or fruits and/or seeds and/or plant cells, characterised in that it contains a lactoferrin, particularly a human lactoferrin or a derived protein, according to the invention, these plants being particularly chosen from amongst rape, tobacco, maize, peas, tomatoes, carrots, wheat, barley, potatoes, soy, sunflower, lettuce, rice, alfalfa and beets.

the used of plants, plant extracts or parts of plants according to the invention, and/or proteins (lactoferrin, particularly human lactoferrin, or derived proteins) according to the invention, for the production of pharmaceutical, medical, odontological, cosmetic or biotechnological compositions, a biomaterial or a pharmaceutical, medical, odontological, cosmetic or biotechnological composition characterised in that this comprises plants, plant extracts or parts of plants according to the invention, and/or proteins (lactoferrin, particularly human lactoferrin, or derived proteins) according to the invention.

A pharmaceutical composition according to the invention includes particularly any composition according to the invention which constitutes or is used in the manufacture of a composition allowing for the detection or treatment of a pathology or a symptom of bacterial, fungal or viral origin, an inflammation or a pathology having an inflammatory component, septic shocks, a pathology related to a cellular growth phenomenon or an iron deficit, such as anaemia.

A cosmetic composition according to the invention includes particularly any composition according to the invention constituting (or used in the manufacture of) an additive for preparations (creams, ointments, makeup, salves).

Advantageously, the recombinant sequences according to the invention contain one (or several) sequence(s) which code for a peptide responsible for addressing recombinant polypeptides in a specific compartment of the plant cell, particularly in the endoplasmic reticulum or in the vacuoles, or even outside the cell in the pectocellulosic wall or in the extracellular space know as the apoplasm.

Amongst the transcription terminators which can be used for the transformation of plant cells within the framework of the present invention, examples include terminator polyA 35S of the cauliflower mosaic virus (CaMV), or the terminator polyA NOS, which corresponds to the non-coding 3' region of the nopaline synthase gene of the plasmid TI of the nopaline strain of *Agrobacterium tumefaciens*.

Accordingly, the invention takes as its object any recombinant nucleotide sequence such as described above which contains the terminator polyA 35S of the CaMV, or the terminator polyA NOS of *Agrobacterium tumefaciens* downstream of said cDNA or a derived sequence thereof.

Amongst the transcription promoters which can be used for the transformation of plant cells in the framework of the invention, examples include:
- the promoter 35S (P35S), or advantageously the double constitutive promoter (Pd35S) of the CaMV: these promoters allow for expression of the recombinant polypeptides of the invention in the entire plant produced from transformed cells according to the invention, and are described in the article of Kay et al., 1987,
- the promoter PCRU of the radish cruciferin gene allows for the expression of the recombinant polypeptides of the invention in only the seeds (or grains) of the plant produced from transformed cells according to the invention and is described in the article by Depigny-This et al., 1992;
- the promoters PGA1 and PGA6, which correspond to the non-coding 5' region of the seed reserve protein genes, GEA1 and GEA6 respectively, of *Arabidopsis thaliana* (Geubier et al., 1993) allow for specific expression in seeds,
- the chimeric promoter super-promoter PSP (Ni M. et al., 1995), which is constituted from a triple repetition of a transcription activation element of the *Agrobacterium tumefaciens* octopine synthase gene promoter, of a transcription activation element of the mannopine synthase gene promoter, and of the mannopine synthase promoter of *Agrobacterium tumefaciens*,
- the rice actin promoter followed the actin intron (PAR-IRA) contained in the plasmid pAct1-F4 described by McElroy et al., (1991),
- the barley HMWG (high molecular weight glutenin) promoter (Anderson O. D. et al., 1989),
- the maize γzein gene promoter (Pγzein) contained in plasmid pγ63 described in Reina et al., (1990) which allows for expression in the albumen of maize seed.

Accordingly, the object of this invention extends to any recombinant nucleotide sequence such as described above containing the double 35S constitutive promoter (Pd35S) of the CaMV, the promoter PCRU of the radish cruciferin gene, the promoters PGA1 or PGA6 of *Arabidopsis thaliana*, the chimeric promoter super-promoter PSP of *Agrobacterium tumefaciens*, the rice PAR-IRA promoter, the wheat HMWG promoter, or the maize Pγzein promoter, upstream of said cDNA or a sequence derived therefrom.

Sequences coding for an addressing peptide in the framework of the present invention may be of plant, human or animal origin.

Amongst sequences coding for an addressing peptide originating in plants, examples include:
- the nucleotide sequence of 69 nucleotides (shown in the examples which follow) which codes for the 23 amino acid prepeptide (signal peptide) of sporamin A in sweat potatoes, this peptide signal allows the recombinant polypeptides of the invention to enter the secretion system of the plant cells transformed according to the invention (that is to say, principally in the endoplasmic reticulum),
- the nucleotide sequence of 42 nucleotides (shown in the examples which follow) which codes for the vacuolar addressing N-terminal propeptide of 14 amino acids of sweet potato sporamin A, which allows for the accumulation of recombinant polypeptides according to the invention in the vacuoles of plant cells transformed according to the invention,
- the nucleotide sequence of 111 nucleotides (shown in the examples which follow) which codes for the prepropeptide of 37 amino acids of sporamin A comprising the N-terminal part nearest the C-terminal part comprising the 23 amino acids of the aforementioned signal peptide, followed by the 14 amino acids of the aforementioned propeptide: this prepropeptide allows for entry of the recombinant polypeptides of the invention in the secretion system, and their accumulation in the vacuoles of the plant cells transformed according to the invention; the three aforementioned sequences are described in the articles of Murakami et al., 1996, and Matsuoka et al., 1991,
- the barley lectin carboxy terminal propeptide, particularly as described in the articles of Schroder et al., 1993, and Bednarek et al., 1991,
- and PRS (pathogenesis related protein, Corenlissen et al., 1986) which allows for secretion.

Amongst sequences which code for an addressing peptide, examples also include those coding for the peptides KDEL (SEQ ID NO: 1), SEKDEL (SEQ ID NO: 2) and HDEL (SEQ ID NO: 3), and allowing for addressing in the endoplasmic reticulum.

The object of the invention also extends to any recombinant nucleotide sequence such as described above which contains a sequence coding for all, or part, of a vacuole addressing peptide, particularly that of sweat potato sporamin A; where this sequence codes for a vacuole addressing peptide which is located, in said recombinant nucleotide sequence, between the sequence coding for a signal peptide and that coding for said cDNA or a derived sequence thereof, in such a way that the first N-terminal amino acid of the vacuole addressing peptide is joined to the last C-terminal amino acid of the signal peptide, and wherein the last C-terminal amino acid of said addressing peptide is joined to the first N-terminal amino acid of the polypeptide coded by said cDNA or a derived sequence thereof, in the protein coded by said recombinant nucleotide sequence.

The object of the invention also extends to any nucleotide sequence such as described above which contains a sequence which codes for all or part of a vacuole addressing peptide, particularly that of barley lectin, wherein this sequence codes for a vacuole addressing peptide which is located upstream of the sequence coding for said cDNA or a derived sequence thereof, so that the first N-terminal amino acid of the vacuole addressing peptide is joined to the last C-terminal amino acid of the polypeptide coded by said cDNA or a derived sequence thereof, in the protein coded by said recombinant nucleotide sequence.

Example 1

Construction of the pBS-Lf Plasmid Containing the Entire cDNA Coding for Human Lactoferrin Lactoferrin is synthesised in the form of a pre-protein in which the sequence coding for the mature 692 amino acid protein is preceded by a 19 amino acid signal peptide (PSLf, having the sequence MKLVFLVLLFLGALGLCLA (SEQ ID NO: 4).

The entire cDNA containing the signal peptide sequence was used in this example. It was isolated from a human mammary gland cDNA bank (Clontech, item HL1037b, CA, USA) constructed in the vector λgt11. Screening of the bank was carried out with an oligonucleotide probe corresponding to the amino acids of the signal peptide (that is to say, amino acids 1 to 19 of the immature hLf, also known as human prelactoferrin) of Lf by means of the nitro-cellulose replica hybridisation method. Briefly stated, the clones are fixed in a NaOH 0.5 M, NaCl 1.5 M bath for two minutes and then neutralised for 5 minutes in a NaCl 1.5 M, Tris-HCl 0.5 M, pH 7.4 solution. The filters are then rinsed with 2×SSC (17.5 g/l NaCl, 8.8 g/l trisodium citrate, QSP 1l). Lastly, the DNA is fixed by heat treatment at 80° C. for 2 hours. The hybridisation was carried out using the oligonucleotide probe described above, labelled at $^{32}$P, with $10^6$ cpm/ml of hybridisation solution (6×SSC, 10×Denhardt, 0.1% (w/v) Nonidet NP40 (octyl phenoxypolyethoxyethanol, Sigma), 100 μg/ml of salmon sperm DNA) overnight at 65° C. The replicas were then washed 4 times in a 2×SSC solution, 0.1% SDS at 42° C., then exposed.

By means of controlled hydrolysis of λgt11 by EcoRI (3 U/μg of DNA for 2 min. at 37° C.) the entire Lf cDNA was cloned in the plasmid pBluescript SK (Stratagene, La Jolla, USA) at the EcoRI site, thus producing the plasmid pBS-Lf.

Example 2

Construction of a pBS-12 Plasmid Containing the Entire cDNA Coding for Human Lactoferrin, Modified at its 3' Extremity The cDNA was modified at 3' so as to be able to join the sequence situated downstream of the stop codon with the terminator contained in pBIOC21, described below. Using PCR, this modification made it possible to remove the natural EcoRI restriction site (GAATTC) located upstream of the stop codon, and to create one, 9 base pairs downstream, followed by a XbaI site (TCTAGA).

This PCR on the pBS-Lf matrix was carried out using the following set of oligodeoxynucleotides:

oligo 5': 5' ATGACAACACTGAGTGTCTGGCC 3' (SEQ ID NO: 5) (corresponding to nucleic acids 1991 to 2011, that is to say, to amino acids 644 to 671 on the immature hLf) oligo 3': 5' CCGTCTAGAGAATTCGTTTTACTTCCT-GAGGGAGTTCAC 3' (SEQ ID NO: 6) which contains the mutation sites (oligonucleotide overlapping the stop cordon, corresponding to amino acid 711 of the immature hLf).

PCR Conditions:

The reagents used in the various PCRs were provided by Promega (Charbonnière, France). The oligodeoxynucleotides were synthesised by Eurogentec (Seraing, Belgium). In each case, 5 ng of matrix were incubated in the presence of 100 pmol of each of the two oligodeoxynucleotides, 3 μl of dNTP 10 nM, 6 μl of MgCl$_2$ 25 nM, 0.5, μl (2.5 U) of Taq DNA polymerase, for a final volume of 100 μl, including the supplier's buffer.

The PCR was carried out with a bio-med THERMOCYCLER 60 (B. Braun). The first denaturation took place for 5 minutes at 94° C. This was followed by 30 cycles each comprising 1 minute at 94° C., 1 minute at (Tm-10° C., that is 50° C.) and 1 minute at 72° C.

The product of the PCR contained a single NdeI site (amino acid 678 of the immature hLf) of lactoferrin cDNA. This fragment was hydrolysed by XbaI and NdeI and sub-cloned to pBS-Lf with the NdeI-XbaI fragment deleted, which resulted in the production of the plasmid pBS-12.

Ligation conditions were as follows: 100 ng of plasmid and 100 ng of inserts were incubated overnight at 16° C. in the presence of 4 U of T4 DNA ligase (Strategene) in the buffer and under the conditions recommended by the supplier; that is, in a final volume of 50 μl containing, amongst other things, 1 μl of 10 mM ATP. These conditions were used for all the ligation reactions described hereafter.

The product of the ligation was used to transform DH5α bacteria, which had been made competent beforehand using the Rubididum method described below.

Preparation of Competent Bacteria:

1 ml of the night culture of DH5α was recultured in a LB medium (10 g/l bactotryptone (g/l of yeast extract, 5 g/l of NaCl) containing KCl (250 mM) and MgSO4 (16 mM) until a DO$_{650}$ of 0.3 was obtained. The bacteria suspension was then centrifuged at 2500 rpm for 5 minutes at 4° C.; the pellet was resuspended in a Tfb1 solution (RbCl 100 mM, MnCl$_2$ 10 mM, glycerol 15%, pH 5.8 adjusted with HOAc 0.2 M), incubated on ice for 15 minutes, then centrifuged again under the same conditions. This time, the pellet was resuspended in 6.5 ml of buffer Tfb2 (MOPS 10 mM, RbCl 10 mM, CaCl$_2$ 75 mM, glycerol 15%, pH 7 adjusted with NaOH 0.5 M). The cells were then portioned at 200 μl per tube and stored at -80° C. for the following transformation processes.

At the time of the transformation process, the cells were thawed on ice and the DNA solution (25 μl of the ligation reaction, that is 50 ng of DNA) was added to 200 μl of competent DH5α. The suspension was incubated on ice for 20 minutes, then plunged into a bath a 42° C. for 90 seconds before returning it to the ice for 5 minutes. The suspension was recultured in a liquid LB medium for 1 hour, then spread on a LB medium containing the selection marker. Following one night of culturing at 37° C., the clones were analysed.

This method was used for all the successive transformations.

After analysing the pBS12 clones, the sequence of the fragment, which was amplified by means of PCR, was confirmed by sequencing (Sanger et al., 1975) of this plasmid (Sequenase DNA Sequencing Kit, United States Biochemical Corporation, Cleveland, USA).

Example 3

Construction of the Plasmid pBS-14, derived from pBS-12, Comprising the cDNA Coding for Human Lactoferrin wherein the Signal Peptide (PSLf) has been Replaced by that of the Signal Peptide of Sweet Potato Sporamin (PSSp)

Firstly, a SalI site was introduced downstream of XhoI in the cDNA of Lf at the first codon of the mature protein sequence, so as to be able to join this with the sequence coding the sweet potato sporamin signal peptide (PSSp; Murakami et al., 1986; Matsuoka et al., 1991) allowing, in theory, for secretion. The sweet potato sporamin signal peptide comprises 23 amino acids in the sequence MKAFTLAL-FALSLYLLPNPAHS (SEQ ID NO: 7).

The oligodeoxynucleotides, oligo 5': 5' TAACTCGAGGC-CGGGTCGACGGAGAAGGAGTGTTCAGTG 3' (SEQ ID NO: 8) containing SalI (GTCGAC) and XhoI (CTCGAG); amino acids 16 to 28 of the immature hLf, and, oligo 3': 5' ACCCGTCCAATTCAAGAATGGACGAAG 3' (SEQ ID NO: 9) containing XcmI (CCAATTCAA-GAATGG (SEQ ID NO: 10), amino acid 153 of the immature hLf), were used for this PCR on the pBS-12 matrix, the conditions for which are described above. The fragment produced by the PCR was hydrolysed by XhoI and XcmI. It was inserted at the XhoI and XcmI sites of pBS-12 using the ligation conditions described above. The transformation was carried out as described above. The resulting plasmid was called pBS-13. The sequence thereof was verified by sequencing as described above.

Secondly, in order to join the cDNA of the signal peptide with that of mature Lf, a SalI site (GTCGAC) was introduced by means of PCR at the last codon of the sporamin peptide sequence, as well as a XhoI site (CTCGAG) followed by an EcoRI site immediately upstream of the ATG initiation codon. These modifications were carried out using PCR on a pMAT103 matrix, according to the conditions described above. The oligodeoxynucleotides chosen allowed for the insertion of the following restriction sites: oligo 5': 5' TCCCTCGAGGAATTCATGAAAGCCTTCACACTC 3' (SEQ ID NO: 11) and, oligo 5': 5' TCCGTCGACCG-GAATGGGCTGGATTGGGCAGC 3' (SEQ ID NO: 12)

After digestion of the fragment, amplified by XhoI and Sal L, this was sub-cloned in pBS-13 which had been hydrolysed beforehand by XhoI and SalI. The resulting pBS-14 plasmid was verified by sequencing the first 500 nucleotides of the chimeric protein.

Example 4

Construction of pBIOC21

Expression of the cDNA coding for lactoferrin in tobacco leaves and seeds required the following regulatory sequences:
1. the double 35S constitutive promoter (Pd35S) of the CaMV (cauliflower mosaic virus). This consists of a duplication of the sequences which activate transcription and which are located upstream of the TATA element of the natural 35S promoter (Kay et al., 1987);
2. the transcription terminator sequence, terminator polyA 35S (T35S), which corresponds to the non-coding 3' region of the double-stranded circular DNA cauliflower mosaic virus producing the 35S transcript (Franck et al., 1980).

The constructions of the various plasmids via recombinant DNA methods derive from pBIOC4. The binary plasmid derives from pGA492 (An, 1986). The plasmid deriving from pBIOC4 and containing the expression cassette "PD35S-T35S" is the plasmid pBIOC21.

The various elements allowing for the reproduction of these constructions are, for example, included in the description of patent application WO9633277, which is incorporated by way of reference.

Example 5

Construction of pBIOC21-PSLf-Lf

Plasmid pBS-12 was hydrolysed by EcoRI to isolate the 2160 base pair fragment corresponding to the sequence which codes for human lactoferrin, preceded by its natural signal peptide. This fragment was sub-cloned in the binary plasmid pBIOC21 which had been EcoRI linearised and dephosphorylated. The binary plasmid produced was called pBIOC21-PSLf-Lf.

The dephosphorylation reaction was applied to 800 ng of DNA in the presence of 1 U of CIP (Stratagene) in the supplier's buffer at a volume of 40 µl for 30 minutes at 37° C. The ligation and transformation reactions for the DH5α strain of *Escherichia coli* were carried out as mentioned above.

The plasmid DNA of pBIOC21-PSLf-Lf was introduced to the strain LBA4404 of *Agrobacterium tumefaciens* according to the Holsters (1978) method. The clones retained were verified by enzymatic digestion of the plasmid DNA introduced.

Example 6

Construction of pBIOC21-PSSp-Lf

The DNA coding for the chimeric protein "PSSp-Lf" was excised from pBS-14 by means of hydrolysis with EcoRI. This 2150 base-pair coding fragment was sub-cloned at the dephosphorylated pBIOC21 EcoRI site. The binary plasmid produced was called pBIOC21-PSSp-Lf.

The dephosphorylation, ligation and transformation reactions for the DH5α strain of *Escherichia coli* were carried out as above.

The plasmid DNA of pBIOC21-PSSp-Lf was introduced to the strain LBA4404 of *Agrobacterium tumefaciens* according to the Holsters (1978) method. The clones retained were verified by enzymatic digestion of the plasmid DNA introduced.

Example 7:

Construction of pACT-IA-PSLf-Lf

Constitutive expression in maize seed required the following regulatory sequences.
- rice actin promoter followed by the rice actin intron (pAR-IAR) contained in the plasmid pAct1-F4, described by McElroy et al., (1991)
- the transcription terminator sequence, terminator polyA NOS, which corresponds to the non-coding 3' region of the nopaline synthase gene of the Ti plasmid of nopaline strain *Agrobacterium tumefaciens* (Depicker et al., 1982).

The plasmid pBSII-pAR-IAR-tNOS in which the coding sequence "PSLf-Lf" was introduced is described, for example, in patent application WO9633277, which is incorporated by reference.

The coding sequence "PSLf-Lf" was isolated from pBS-12 by means of enzymatic digestion by Eco-RI. The digested fragment was purified by means of electrophoresis on 0.8% agarose gel, electro-eluted, alcohol precipitated, dried, and resuspended in $H_2O$. It was treated with Klenow enzyme (New England Biolabs) according to the manufacturer's recommendations. It was inserted in the plasmid pBSII-pAR-IAR-tNOS, double digested by SalI and NcoI, purified, treated with Mung Bean Nuclease (New England Biolabs) and dephosphorylated by the veal alkaline phosphatase enzyme (Boehringer Mannheim) in accordance with the recommendations of the manufacturer. Ligation was carried out with 20 ng of the dephosphorylated vector and 200 ng of DNA fragments containing the sequence coding for "PSLf-Lf", described above, in a reaction solution of 20 μl, in the presence of 2 μl of T4 DNA ligase×10 buffer (Amersham), 2 μl of 50% polyethylene glycol 8000 and 5 U of T4 DNA ligase (Amersham) at 14° C. for 16 hours. DH5α strain *Escherichia coli* bacteria which had been made competent beforehand were transformed (Hanahan, 1983). The plasmid DNA of the clones produced, which were screened with 50 μg/ml ampicillin, was extracted using the alkaline lysis method (Birnboim and Doly, 1979) and analysed by means of enzymatic digestion by restriction enzymes. The plasmid produced was called pACT-IA-PSLf-Lf.

Example 8

Construction of pACT-IA-PSSp-Lf

The construction of pACT-IA-PSSp-Lf is similar to that of pACT-IA-PSLf-Lf, except that the sequence "PSLf-Lf" is replaced with that coding for "PSSp-Lf", corresponding to the EcoRI fragment treated with the Klenow enzyme (New England Biolabs), isolated from pBS-14. The resulting plasmid was named pACT-IA-PSSp-Lf.

Example 9

Construction of pgzein-PSLf-Lf

Expression in the albumen of maize seed required the following regulatory sequences:
the maize zein gamma (g) gene promoter (Pgzein) contained in the plasmid p63, described by Reina et al., 1990. Plasmid p63 is the result of cloning Pgzein to replace the 35S promoter (P35S), at the HindIII and XbaI sites of plasmid pUC18, which contains, between its HindIII and EcoRI sites, the expression cassette "P35S-gus-TNOS" of pBI221, which is marketed by Clontech. It allows for expression in the albumen of maize seed.
the transcription termination sequence, terminator polyA NOS, which corresponds to the non-coding region of the nopaline strain *Agrobacterium tumefaciens* Ti plasmid nopaline synthase gene (Depicker et al., 1982).

The plasmid pgzein-PSLf-Lf where the sequence "PSLf-Lf" is placed under the control of Pgzein was produced by cloning at the sites SacI and BamHI, treated by the enzyme T4 DNA polymerase (New England Biolabs), then dephosphorylated by the veal alkaline phosphatase enzyme (Boehringer Mannheim) of plasmid p63, of the EcoRI fragment treated with Klenow (New England Biolabs) isolated from pBS-12. Ligation was carried out as described in Example 7. The DH5α, *Escherichia coli* bacteria, which had been made competent beforehand, were transformed (Hanahan, 1983). The plasmid DNA of the clones produced, which were screened with 50 μg/ml ampicillin, was extracted using the alkaline lysis method (Birnboim and Doly, 1979) and analysed by means of enzymatic digestion by restriction enzymes. The plasmid produced was called pgzein-PSLf-Lf.

Example 10

Construction of pgzein-PSSp-Lf

The construction of pgzein-PSSp-Lf is similar to that of pgzein-PSLf-Lf, except that the sequence "PSL-Lf" is replaced with that coding for "PSSp-Lf", corresponding to the EcoRI fragment treated with the Klenow enzyme (New England Biolabs), isolated from pBS-14. The resulting plasmid was named pgzein-PSSp-Lf.

Example 11

Construction of pHMWG-IA-PSLf-Lf

Expression in maize seed required the following regulatory sequences:
the wheat HMWG (high molecular weight glutenin) promoter (Anderson et al., 1989) followed by the rice actin intron,
the transcription terminator sequence, terminator polyA 35S (T35S), which corresponds to the non-coding 3' region of the double-stranded circular DNA cauliflower mosaic virus producing the 35S transcript (Franck et al., 1980). The pHMWG-IA plasmid results from cloning PHMWG-IA in place of the promoter PD35S (P35S) of the plasmid pJIT163. The various elements allowing for this construction to be reproduced are, particularly, described in international patent application No. WO 96/33277.

The plasmid pHMWG-IA-PSLf-Lf where the sequence "PSLf-Lf" is placed under the control of pHMWG-IA was produced by cloning at the EcoRI site, dephosphorylated by the veal alkaline phosphatase enzyme (Boehringer Mannheim), of plasmid pHMWG-IA, of the EcoRI fragment isolated from pBS-12. Ligation was carried out with 100 ng of the dephosphorylated vector and 50 ng of DNA fragments containing the sequence coding for "PSLf-Lf", described above, in a 10 μl reaction solution, in the presence of 1 μl of T4DNA ligase tampon (Amersham) at 14° C. The DH5α *Escherichia coli* bacteria, which had been made competent beforehand, were transformed (Hanahan, 1983). The plasmid DNA of the clones produced, which were screened using 50 μg/ml ampicillin, was extracted using the alkaline lysis method, and analysed by means of enzymatic digestion by restriction enzymes. The plasmid produced was called pHMWG-IA-PSLf-Lf.

Example 12

Construction of pHMWG-IA-PSSp-Lf

The construction of pHMWG-IA-PSSp-Lf is similar to that of pHMWG-IA-PSLf-Lf, except that the sequence "PSLf-Lf" is replaced with that coding for "PSSp-Lf", corresponding to the EcoRI fragment isolated from pBS-14. The resulting plasmid was named pHMWG-IA-PSSp-Lf.

Example 13

Production of Transgenic Solanaceous Plants

A. Transformation of Tobacco Plants

The tobacco plants used for the transformation experiments (*Nicotiana tabacum* var. Xanthi NC) were cultivated in vitro on a Murashige and Skoog (1962) basic medium to which the vitamins of Gamborg et al., (1968, Sigma item M0404), 20 g/l of saccharose, and 8 g/l of agar (Merck) were added. The pH of the medium was adjusted to 5.8 with a potassium solution before autoclaving at 120° C. for 20 minutes. The tobacco plantlets were replanted from intra-node cuttings each 30 days into this multiplication medium MS20 (M0404 at 4.4 g/l, saccharose at 20 g/l, agar agar at 8 g/l, pH 5.7).

All of the in vitro cultures were carried out in climate-controlled enclosures, under the following conditions:
  luminous intensity of 30 µE $m^{-2} \cdot S^{-1}$; photoperiod of 16 hours;
  thermoperiod of 26° C. in the day and 24° C. at night.

The transformation method used was derived from that of Horsch et al., (1985).

A pre-culture of LBA4404 strain *Agrobacterium tumefaciens* containing the binary plasmids was carried out for 48 hours at 28° C., under agitation, in an LB medium to which suitable antibiotics (rifampicin and tetracycline) were added. The pre-culture was then diluted by a factor of 50 in the same medium and cultivated under the same conditions.

After one night, the culture was centrifuged (10 min., 3000 g), the bacteria were resuspended in an equivalent volume of liquid MS30 medium (M0404 at 4.4 g/l, saccharose at 30 g/l, pH 5.7) and this suspension was diluted by a factor of 10.

Explants of approximately 1 $cm^2$ were cut from the plantlets described above. These were then placed in contact with the bacterial suspension for 1 hour, then quickly dried on filter paper and placed in a coculture medium (solid MS30 consisting of liquid MS30 to which agar agar at 8 g/l, BAP 1 mgA and ANA at 0.1 mg/l had been added).

Two days later the explants were transferred to Petri dishes on an MS30 regeneration medium (consisting of the coculture medium to which kanamycin at 200 mgA and Augmentin at 400 mgA had been added). This medium contains a selection agent, kanamycin (200 mg/l), a bacteriostatic, Augmentin (400 mg/l) and the hormones necessary to induce buds (BAP, 1 mg/l and ANA, 0.1 mg/l). The explants were replanted in the same medium after 2 weeks of culture. After a further two weeks, the buds were replanted into Petri dishes in the development medium consisting of MS20 medium to which kanamycin and Augmentin had been added. Fifteen days later, half the buds were replanted. It takes approximately 20 days for roots to form. At the end of this period, the plantlets can be cloned by way of inter-node cuttings, or can be put in a greenhouse.

B. Production of Transgenic Tomato Plants cv. UC82B tomato seeds were sterilised with 10% Domestos for 15 minutes and rinsed 3 times in sterile water. The last rinse is carried out for 10 minutes, under agitation.

Seeds rinsed in this manner were allowed to germinate in a MSSV/2 medium (basic Murashige and Skoog medium (1962, Sigma item M6899)/2 to which the vitamins of Nitsch (Thomas and Praqtt, 1981), 30 g/l of saccharose, and 8 g/l of agar (Merck) were added, pH 5.9), for 7 to 8 days in a climate controlled chamber (luminous intensity of 30 µE $m^{-2} \cdot S^{-1}$; photoperiod of 16 h/8 h, 26° C.).

The transformation method used is derived from that of Fillatti et al., (1987).

A pre-culture of LBA4404 strain *Agrobacterium tumefaciens* containing the binary plasmids was carried out for 48 hours at 28° C., under agitation, in an LB medium to which suitable antibiotics (rifampicin and tetracycline) were added. The pre-culture was then diluted by a factor of 50 in the same medium and cultivated under the same conditions for one night. The DO at 600 nm was measured, the *agrobacteria* were centrifuged (10 min., 3000 g), resuspended in a liquid KCMS medium (described in the publication of Filledtti et al., 1987) so as to obtain a DO of 0.8 at 600 nm.

Technical improvements were made to certain processes within the method of Fillatti et al., (1987). The pre-culture of the explants and the coculture are as described by Filliatti et al., (1987) except that acetosyringon (200 nM) is added to the KCMS medium.

The 2z washing medium differs in that cefotaxime is added at 500 mg/l, in place of carbenicillin. The development medium used is composed of the basic Murashige and Skoog medium (1962, Sigma item M6899) to which the vitamins of Nitsch, 20 g/l of saccharose, 50 mg/l of kanamycin, 200 mg/l of Augmentin, 1 mg/l of ANA, and 0.5 mg/l of zeatin was added.

Example 14

Production of Transgenic Rape Plants

Spring rape seed (*Brassica napus* cv WESTAR or Limagrain strains) were disinfected for 40 minutes in a 15% Domestos solution. After 4 rinses in sterile water, the grains were allowed to germinate in pots of 7 cm in diameter and 10 cm in height with 7 seeds to a pot, in the Murashige and Skoog mineral medium (Sigma M 5519) with 30 g/l of saccharose, solidified with 5 g/l of agar gel. These pots were placed in a culture chamber at 26° C. with a photoperiod of 16 h/8 h and a luminous intensity in the order of 80 $\mu m^{-2} s^{-1}$.

After 5 days of germination, the cotyledons were removed in a sterile manner, cutting each petiole approximately 1 mm above the cotyledon node.

At the same time, a pre-culture of strain LBA4404 of *Agrobacterium tumefaciens* containing the binary plasmid was prepared in a 50 ml Erlenmeyer flask, for 36 hours, in 10 ml of 2YT bacterial culture, to which the antibiotics used in the selection of the chosen strain were added.

This pre-culture was used to seed a new bacterial culture at 1%, prepared under the same conditions. After 14 hours, the culture was centrifuged for 15 minutes at 3000 g, and the bacteria were resuspended in an equivalent volume of liquid germination medium. This suspension was portioned into Petri dishes of 5 cm in diameter at 5 ml/dish.

The cut-end of a petiole was immersed in the solution of *agrobacteria* thus prepared for a few seconds, then the petiole was pushed a few millimeters into the regeneration medium. This medium has the same basic composition as the germination medium but 4 mg/l of benzyl-amino-purine (BAP), a phyto-hormone which encourages the formation of new buds, was added. Ten explants (cotyledon with petiole) were cultured in each 9 cm diameter Petri dish (Greiner item 664102).

After two days of coculture under the same environmental conditions as used for germination, the explants were replanted in Phytatray trays (Sigma, item P1552) containing the same medium as before, to which a selection agent: 45 mg/l of kanamycin sulphate (Sigma, item K4000) and a bacteriostatic: a mixture (by weight) of ⅙ potassium clavulanate and ⅚ sodium amoxicillin (injectable Augmentin) were added at 600 mg/l.

Twice thereafter, at intervals of 3 weeks, the explants were replanted in a sterile manner into new culture under the same conditions.

The green buds which appear after two or three replantings were separated from the explant and cultured individually in transparent pots of 5 cm in diameter and 10 cm in height containing the same medium as above, but lacking in BAP. After three weeks of culture, the stems of the transformed buds were cut and the buds were replanted in a pot of fresh medium. After three or four weeks, the roots are well enough developed to allow for acclimatisation of the plantlet in a phytoron. The buds which were not green or do not have roots were eliminated. These plants were then transplanted into square pots of 7×7 cm filled with potting soil (NF standard U4455 1: 40% brown peat, 30% sieved soil and 30% sand) saturated with water. After two weeks of acclimatisation in the pytotron (temperature 21° C., photoperiod 16 h/8 h and 84% relative humidity), the plantlets were repotted in pots of 12 cm in diameter, filled with the same potted soil, enriched by timed-release fertiliser (Osmocote, 4 g/l of potting soil) then moved to a greenhouse (class S2) maintained at 18° C., with watering twice a day for 2 minutes per watering.

As soon as flowers appear, these were bagged (Crispac, item SM 570y 300 mm×700 mm) so as to prevent cross fertilisation.

When the siliquas reached maturity, these were gathered, dried, then threshed. The seeds obtained in this manner were used to measure biochemical activity. Selection of transgenic descendants is carried out by germination in a medium containing 100 to 150 mg/l of kanamycin sulphate (depending on genotype). The operating conditions were the same as those described above, with the exception of the fact that the germination took place in glass tubes, with only one seed per tube. Only those plants which developed secondary roots within the first three weeks were acclimatised in the phytotron before being moved to the greenhouse.

Example 15

Production of Transgenic Maize Plants

A. Production and Use of Maize Calluses as Objects of Genetic Transformation

Genetic transformation of maize, regardless of the method used (electroporation, *Agrobacterium*, microfibres, particle cannon) requires, in general, the use of cells which are not differentiated in rapid divisions, and thus have conserved the ability to regenerate entire plants. This type of cell makes up the embryogenic friable callus (know as type II) of maize.

These calluses were obtained from immature embryos of genotype H1 II or (A188×B73) according to the method and using the media described by Armstrong (1994). The calluses obtained in this manner were multiplied and maintained by successive replanting each 15 days, in the initiation medium.

Plantlets were regenerated from these calluses, by modifying the hormonal and osmotic balance of the cells according to the method described by Vain et al., (1989). These plants are then acclimatised in a greenhouse, or they can be crossed or self fertilised.

B. Use of a Particle Cannon for the Genetic Transformation of Maize

The pervious section describes the production and regeneration of the cell line required for transformation; a method of genetic transformation allowing for the stable integration of modified genes within the plant genome will be described here. This method is based on the use of a particle cannon, and is the same as that described by J. Finer (1993). The target cells are callus fragments as described in paragraph 1. Four hours before bombardment, 16 fragments per dish of these fragments, having a surface area of 10 to 20 $nm^2$, were placed in the centre of Petri dishes containing the same medium as the initialisation medium, to which 0.2 M of mannitol+0.2 M of sorbitol were added. The plasmids bearing the genes to be introduced were purified with a Qiagen column according to the manufacturer's instructions. They were then precipitated on tungsten particles (M10) according to the method described by Klein (1987). Particles coated in this manner were fired at the target cells, using a cannon according to the method described by J. Finer (1992).

The dishes of calluses which had been bombarded in this manner were then sealed with Scellofrais, and cultivated in the dark at 27° C. The first replanting was performed 24 hours later, then every 15 days for a period of three months, using the same medium as the initiation medium, to which a selection agent was added, the nature and concentration of which varies with the gene used (see paragraph 3). The selection agents which can be used generally consist of the active ingredients of certain herbicides (Basta™, Round Up™) or certain antibiotics (Hygromycin, Kanamycin, etc.).

After 3 moths, or sometimes earlier, the calluses which are not inhibited in terms of growth by the selection agent, normally, and in the majority of cases, composed of cells resulting from the division of a cell which has integrated one or more copies of the selection gene in its genetic heritage, appear. The frequency with which such calluses are obtained was approximately 0.8 calluses per bombarded dish.

These cells were identified, individualised, amplified and then cultivated, so as to regenerate plantlets (cf. Paragraph A, Example 15). In order to avoid all possible interference by non-transformed cells, all of these operations were carried out in culture media containing the selection agent.

The plants regenerated in this manner were acclimatised, then cultivated in greenhouses where they could be crossed or self-fertilised.

The plants obtained according to the invention have a phenotype distinct from that obtained in WO9637094.

Example 16-a

Detection of Recombinant Human Lactoferrins (rhLf) from Plant Leaves

In order to test for the most productive plants, soluble proteins was carried out on twenty transformation products for each of the constructions, pBIOC21-PSLf-Lf and pBIOC21-PSSp-Lf, followed by demonstration of the quality and quantity of the recombinant Lf (rhLf) present. The leaves were ground in liquid nitrogen until a fine powder was obtained. The soluble proteins were extracted from the vegetal matter using an extraction solution (Tris-HCl 50 nM, EDTA 1 mM, NaCl 100 mM, Triton X 100 0.1%, pH 6.5) at a ratio of 4 ml of solution per gram of leaf. After centrifuging the extract for 30 minutes at 13,000 g, the supernatant was decanted, filtered and used for the following processes in the demonstration of the presence of recombinant lactoferrin.

ELISA Method of Lactoferrin Detection (Micogami et al., 1994)

Selection of a transformant for each type of molecular construction was carried out by comparing the quantity of recombinant Lf with the quantity of soluble proteins. Quantification of soluble proteins was performed using microtitration (Promega, Charbonnière, France), and the rate of expression of rhLf was measured using the ELISA method described hereafter.

A polyclonal rabbit anti-human lactoferrin antibody was produced as follows: immunisation of the rabbit was produced by three successive intramuscular injections of hLf. For the first injection, 1 mg of hLf dissolved in 0.25 ml of nonpyrogenic physiological serum and 0.25 ml of complete Freund adjuvant (Difco) were injected. Two weeks later, a second injection was performed with 1 mg of hLf dissolved in 0.25 ml of nonpyrogenic physiological serum and 0.25 ml of incomplete Freund adjuvant (Difco). Four weeks later, a third injection was performed under the same conditions as the second. The first blood sample was taken 10 to 15 days after the third injection and produced 20 ml of blood. Thereafter, injections corresponding to booster shots (same conditions as the second injection, described above) allowed for samples to be taken every 10 days. The immunoglobulins of the rabbit antiserum were purified by means of 35% saturated ammonium sulphate precipitation. The precipitate was dialysed in a 10 mM pH 8 TrisHCl buffer then purified by DEAE Trisacryl (IBF) chromatography.

The polyclonal antibodies were incubated in the wells of the microtitration plate, at 100 µl per well (that is, 35 µg/ml), in a sodium bicarbonate buffer (NaHCO3) 10 mM (pH 9.6) overnight at 4° C. or for 2 hours at 37° C.

Incubation of the ELISA plate (Falcon) in 150 µl of PBS (NaCl 150 mM, sodium phosphate (Na2HPO4, NaH2PO4) 50 mM, pH 7.5)-Tween 2% for 20 minutes at room temperature allowed for blocking of the non-specific sites. Following three washes with PBS-Tween 0.05%, 100 µl of each sample resulting from the soluble protein extracts was incubated at 37° C. for 2 hours; following which hLf was detected by the anti-Lf monoclonal antibodies. The anti-Lf monoclonal antibodies were produced by fusing mouse splenocytes and $SP_2O/Ag$ myeloma cells. The supernatant from the hybrid culture medium was used directly in the ELISA test. The Ab-rhLf complex was recognised by caprine anti-mouse antibodies labelled with peroxidase (Pasteur Diagnostics) diluted to 1/3000 in PBS and was placed in contact, as above, for 2 hours at 37° C. Detection was carried out under agitation by addition of the substrate solution (4 mg of ortho-phenylenediamine dihydrochloride in 10 µl of 0.2 mM, pH 5.5 "citric acid/sodium citrate" buffer in the presence of 10 µl of $H_2O_2$), coloration was achieved in a few minutes and the reaction was stopped by adding 50 µl of 20% $H_2SO_4$ per well. Optical density was read at 490 nM.

Between each step, the wells were washed with 0.05% PBS-Tween.

The ratio of rhLf to soluble proteins is shown in FIG. 1. This resulted in the selection of transformant T19 for the construction pBIOC21-PSLfLf, and transformant T30 for the construction pBIOC21-PSSp-Lf.

Analysis of the transformants by the ELISA method also showed a rate of expression of rhLf in the T30 transformant obtained with the construction pBIOC-PSSp-Lf which was 3 times greater than that of the transformant T19, transformed with pBIOC-PSLf-Lf. This result indicates a higher level of expression of rhLf when the protein's natural signal peptide is replaced with that of sporamin.

Western Blot Method

In order to verify the apparent molecular mass of the rhLf of the selected transformants, Western Blot (FIGS. 2 and 3) and immunoprecipitation (FIG. 4) tests were carried out using the soluble protein extracts.

Following electrophoresis using 7.5% SDS-PAGE polyacrylamide gel (20 µg of soluble proteins per well), the proteins were transferred to a nitro-cellulose membrane. This was then incubated in 2% *PBS-Tween, then washed 3 times with 0.05% PBS-Tween. Rabbit polyclonal antibodies were produced by means of purification of a rabbit antiserum by DEAE Trisacryl chromatography. Following dilution to 500° in PBS (that is 7 µg/ml), these were placed in contact with the membrane for 3 hours at 20° C. Thereafter this was washed with 0.05% PBS-Tween. The conjugate, a caprine anti-rabbit IgG (Pasteur Diagnostics) labelled with peroxidase and diluted to 2500° in PBS, was then incubated for 1 hour at 20° C. The membrane was washed three times with PBS again. Final detection was performed by incubating the membrane one last time in 100 ml of PBS in the presence of 40 mg of DAB (3-3'-diaminobenzidine tetrahydrochloride) and 200 µl of $H_2O_2$.

*PBS: 150 mM NaCl, 50 mM Na2HPO4, NaH2PO4, pH 7.5.

As shown in FIG. 2, analysis of plants produced by the first transformation shows a band of an apparent molecular mass of 80 kDa recognised by the anti-Lf antibody. No signal was detected for the non-transformed control, that is *Nicotiana tabacum* var, Xanthi. The presence of rhLf1 was demonstrated in the transformant t19, which confirms the results obtained by ELISA analysis.

FIG. 3 shows a Western Blot of the soluble proteins produced from transformant T30. It demonstrates the presence of rhLf of an apparent molecular mass of 80 kDa which emigrates with Lf isolated from human milk. It should be noted that the rhLf appears as a double band. This doublet is not explained by a modification at the N-terminal sequence level (cf. Example 2).

Immunoprecipitation 6 mg of Sepharose A-Protein (Parmacia) were incubated for 1 hour at room temperature in the presence of rabbit polyclonal anti-human Lf antibodies. These antibodies were produced as described in Example 16. The Sepharose A-Protein beads were recovered by centrifuging, washed 3 times with TBS (Tris-Hcl 20 mM, NaCl 150 mM, pH 8.2) and agitated in 20 ml of soluble protein extract for 2 hours at room temperature. Following 3 washings in TBS, the protein complex was disassociated in a recovery solution (Tris 62.5 mM, SDS 2%, saccharose 10%, β-mercaptoethanol 5%, bromophenol blue 5%), separated with 7.5% SDS-PAGE polyacrylamide gel, and then coloured with Coomassie blue.

FIG. 4 shows that, following immunoprecipitation of the soluble protein extracts of transformant T19, rhLf appears in the form of a doublet of an apparent molecular mass of 80 kDa. The same result is found for transformant T30.

Example 16-b

Detection of Recombinant Human Lactoferrin (rhLf) in Maize Seed

A. Extraction of Proteins from Maize Seed

Maize seed was ground in liquid nitrogen. Thereafter, this was soaked in 5 ml of buffer (Tris-Hcl 100 mM pH 8, EDTA 1 mM, DTT 1 mM, NaCl 250 mM, Triton X100 0.2%) per 500 mg of ground product overnight at 4° C. The homogenate was then centrifuged at 10000 g at 4° C. for 10 minutes. Quantification of the proteins was carried out according to the Bradford method.

B. Immunodetection of Lactoferrin

The extracted proteins were denatured by heating to 95° C. for 5 minutes in the presence of Tris-HCl 50 mM pH 6.8, SDS 4%, saccharose 20%, β-mercaptoethanol 1%, and bromophenol blue 0.01%. The proteins were then separated by electrophoresis on polyacrylamide gel under 10% denatured conditions. After migration, the proteins were transferred to a nitro-cellulose membrane. Lactoferrin was detected using a human lactoferrin antibody produced by rabbits, then a rabbit anti-IgG coupled to alkaline phosphatase.

C. Screening of Maize Seed Transformed with the Construction pHMWG-IA-PSSp-Lf

Amongst the 10 transformants tested, 5 present a positive signal for immunodetection.

Example 17

Example of Purification of Recombinant Human Lactoferrin (rhLf)

The rhLf1 from pBIOC21-PSLf-Lf and the rhLf2 from pBIOC21-PSSp-Lf were purified by means of affinity chromatography using BrCN activated 4B Sepharose gel (Pharmacia Biotech) to which an anti-lactoferrin polyclonal antibody had been joined.

1 ml of gel, fixing approximately 3 mg of antibody, was batch incubated overnight at 4° C. in 100 ml of protein extract, the pH of which had been adjusted to 8.2 using 1 M Tris.

Thereafter, the gel was thoroughly washed with TBS pH 8.2 (Tris-HCl 20 mM, NaCl 150 nM, pH 8.2) followed by 1 M NaCl, pH 8.2 TBS. Elution was carried out with a glycine-HCl 0.2 M, pH 2.4 buffer, in three successive elutions which were analysed on 7.5% polyacrylamide gel.

This method was used for the preparation of rhLf1, with a view to analysis of the N-terminal sequence. Analysis with 7.5% SDS-PAGE polyacrylamide gel of the rhLf1 and rhLf2 purified by this method shows no difference in mass between the two rhLf (FIG. 5).

For the chimeric protein resulting from pBIOC21-PSSp-Lf, a larger scale purification was carried out with a view to deeper analysis of this protein. Using ion exchange chromatography with an SP Sepharose Fast Flow (Pharmacia Biotech) column, equilibrated with an acetate solution of Na 0.2 M pH 7, and a Biopilot type apparatus (Pharmacia bitotech), rhLf2 was eluted with an NaCl gradient of 0 to 1 M. The rhLf2 was found primarily in a fraction eluted at 0.7 M NaCl, as proved by the ELISA tests carried out on all of the fractions collected.

The positive fractions were concentrated by means of ultrafiltration with Centriprep 30 (Amicon, Bevedrly, USA), dialysed against PBS (NaCl 50 mM, Na2HPO4-NaH2PO4 50 mM, pH 7.5) and frozen at −20° C. The purity of the rhLf2 was verified using 7.5% SDS-PAGE polyacrylamide gel.

Example 18

Variant Form of Extraction and Purification of Recombinant Human Lactoferrin

Fresh or frozen tobacco leaves were ground in liquid nitrogen until a fine powder was obtained. The soluble proteins were then extracted from the vegetal matter using an extraction solution (Tris/HCl 50 mM, NaCl 100 mM, EDTA 1 mM, dithiothreithiol 1 mm, Triton X10 0.2% (w/v), phenylmethylsulphonyl fluoride 1 mm, pH 7.0) containing 0.2 g of Diaion Sepabeads SP 825 (Resindion) or Diaipn HP 20 (Supelco) per ml at a rate of 4 ml of solution per gram of vegetal material. The ground product was incubated at 4° C. for 12 hours with magnetic stirring. The purpose of this step is to extract the soluble proteins and to absorb a portion of the vegetal pigments with the hydrophobic resin. The extract was centrifuged for 45 minutes at 15000 g, then the supernatant was filtered with a 0.45 micron Millipore membrane.

The vegetal extract was subjected to chromatography using a mono-S HR10-10 column (Pharmaci Biotech) equilibrated by a 0.2 M pH 7.8 solution of sodium acetate, using a Biopilot type apparatus (Pharmacia Biotech). After passing the extract through the column, a NaCl gradient of 0 to 1 M in the 0.2 M sodium acetate was established in the column for 60 minutes, and the rhLf was found in an eluate fraction at 0.8 NaCl. This fraction was frozen at −20° C.

Example 19

Analysis of the N-Terminal Sequence

Analysis of the N-terminal sequence using the Edman degradation process showed that, for both of the constructions, that is to say, for the proteins rhLf1 and rhL2, the sequence of the first 7 residues is "GRRRRSV" (SEQ ID NO: 13), which corresponds exactly to the N-terminal end of the reference mature human lactoferrin. These results show that joining the signal peptide for sweet potato sporamin secretion or for that of human lactoferrin to the sequence coding for mature human lactoferrin allows for correct cleavage of this signal peptide.

Example 20

MALDI/TOF Mass Spectrometry Analysis

Analysis was performed using a MALDI Vision 2000 laser desorption mass spectrometer (Funnigan MAT, Brenen, Germany). 3 µl of a solution containing 100 pmol of lactoferrin were added to 17 µl of matrix solution containing 10 mg/ml of 2.5 dihydroxybenzoic acid in a water/acetonitrile (30/70) mixture. 1 µl of this product was sent to the target at the same time as a mass calibre (human serotransferrin, Sigma, with a molecular mass of 79590 Da in sinapinic acid). The molecular mass of rhLf2 was 81250 Da, which corresponds to the mass calculated for the polypeptide chain of hLf (76320 Da) to which two glycans of a total mass of 5180 Da are attached. Based on these values, the glycan ratio represents 6.35% of the total mass of the glycoprotein.

Analysis of the glycoprotein monosaccharides was performed using gaseous phase chromatography with a OV 101 capillary column, and by Girdel 300 chromatography. The helium flow was 10 ml/min and the pressure was 0.5 bars. The temperature was set to 120° C. to 240° C. at 2° C./min. The trimethylsilylated derivatives were prepared by methanolysis (Zanetta et al., 1992), by N reacetylation and trimethylsilyation (Kamerling et al., 1975). Analysis shows a ratio of 6.5% of total oses in the glycoprotein. The molar composition is described below.

|  | Fucose | Galactose | Mannose | glucos-amine | Xylose | N-acetyl neuraminic acid |
|---|---|---|---|---|---|---|
| rhLf2 | 1.5 | 0.7 | 3.0 | 3.3 | 0.7 | 0.0 |
| Lfh | 1.3 | 2.1 | 3.0 | 4.0 | 0.0 | 1.8 |

The results obtained suggest rhLf2 glycans with a structure of the type N-acetyl-lactosamine, with a certain heterogeneity in the monosaccharide molar composition. Of particular note is the presence of xylose, the low level of galactose and the absence of N-acetyl neuraminic acid.

Example 21

Jurkat Cell Binding Experiments

Many studies carried out on lymphocytes have shown the presence of specific receptors for lactoferrin on their surfaces.

Their appearance at lymphocyte surfaces has been studied using the mitogen agent, phytohemagglutinin (PHA, Mazurier et al., 1989). This work showed that quiescent lymphocytes do not have receptors for lactoferrin and that phytohemagglutinin induces the emergence of high affinity receptors on the surfaces of circulating lymphocytes, these receptors being synthesised during the first two days of activation. The binding constants and number of binding sites are 80 nM and 200000 nM respectively under PHA activation conditions. This same receptor was recently studied for the Jurkat lymphoblastic strain which allows for stable and reproducible results (Bi et al., 1994). In the rhLf2 binding tests, this Jurkat cell strain was used for testing the biological activity of the recombinant protein.

The T lymphoblastic cells of the Jurkat strain were cultivated in a RPMI 1640 medium (GIBCO, Cergy Pontoise, France) pH 7.4 containing 25 mM of Hepes, 2 mM of L-glutamine, gentamicin (5 mg/ml) in the presence of 10% foetal veal serum which had previously been deactivated by heat in an oven with 5% $CO_2$ at 37° C.

At the subconfluence stage the cells were diluted to a density of $4 \cdot 10^5$/ml for the binding experiments.

100 μg of rhLf was labelled with 0.2 m Ci of $^{125}I$ using iodobeads (Pierce, Rockford, USA) according to the recommendations of the manufacturer. The free iodine was removed by means of gel filtration, using a Sephadex G-25 column equilibrated with PBS (50 mM NaCl, 50 mM Na2HPO4-NaH2PO4, k pH 7.5). The binding experiments were carried out in RPMI containing 0.4% (w/v) of human transferrin, so as to avoid non-specific rhLf2 binding on the cells or on the plastic. Aliquots of 100 ml containing $5 \cdot 10^5$ cells were separated into 1.5 propylene tubes in the presence of labelled rhLf2 at concentrations ranging from 0 to 100 mM.

Non-specific binding was evaluated in the presence of an 100 molar excess of unlabelled Lf. The cells were incubated with the proteins for 1 hour at 4° C. in the presence of 0.01% (w/v) of sodium azide. Lastly, the cells were washed 3 times in 0.5 ml of PBS. Radioactivity was then measured with a Compugamma gamma radiation counter, LKB—Wallac (Turku, Finland).

Binding of rhLf2 labelled with $^{125}I$ to Jurkat T lymphoblastic cells was analysed using the Scatchard method (1949). As shown in FIG. 6, the binding curves for rhLf2 and Lfh isolated from milk are similar. With the range of Lfh used, only one class of receptor was detected on the cell surface, having a dissociation constant of 80.27±33 nM and a number of sites per cell of 124400±36000. On the same cells, hLf binds with a dissociation constant of 89.7±22 nM and a number of sites per cell of 103300±14000.

Thus, the binding test shows that rhLf2 has a configuration very close to that of human milk Lf, as it is recognised with the same parameters on its lymphocytic receptor.

Example 22

Binding of rhLf2 on the Surface of HT29 Cells

Binding of human milk lactoferrin was demonstrated with a enterocytic strain (HT-29) derived from a human colic adenocarcinoma capable of enterocyte differentiation (Mikogami et al., 1994, 1995). This author showed that binding of lactoferrin on its enterocytic receptor is not linked to the degree to which it is saturated in iron, and is specific, that is to say, it does not result from electrostatic or lectin interactions.

The number of sites on HT29 type cells is in the order of $3 \cdot 10^6$ per cell and the Kd is approximately $10^{-6}$M. The HT-29-18C1 clone conforms to these characteristics and was used for the binding of rhLf2, so as to verify its biological activity.

The HT29 cells of the 18C1 clone were cultivated in DMEM (Eurobio, Les Ullis, France) containing 2 mM of L-glutamine and gentamicin (5 mg/l) in the presence of 10% foetal veal serum which had previously been deactivated by heat in an oven with 10% $CO_2$ at 37° C. At this subconfluence stage, the cells were divided and returned to culture in 2 cm² wells, with $2 \cdot 10^4$ cells/cm². Following 21 days of culture, which allowed for enterocyte differentiation, these cells were used for binding tests.

The rhLf2 was labelled with $^{125}I$ as described in example 19. The cells in each well were incubated for 1 hour on ice, in the presence of 0.01% (w/v) of sodium azide and human transferrin, which prevents non-specific binding by the lactoferrin. The radioactivity of a 50 μl dose was measured for calculation of the concentration of free ligands presented to the cells. Following 5 rinses with 500 μl of DPBS+ (Sigma, ref. D1283), the cells were released by 200 μl of DPBS+/EDTA (5 g/l) and the radioactivity of the rhLf2 bound was measured by a Compugamma λ radiation counter, LKB-Wallac.

Binding of $^{125}I$ labelled rhLf2 to HT-29-18C1 enterocytic cells was analysed by the Scatchard method. As shown in FIG. 7, the binding curves for rhLf2 and Lf isolated from milk are similar. With the range of lactoferrins used, only one class of receptors was detected on the surface of the cells, having a dissociation constant of 0.8±0.19 μM, and $1.8 \times 10^6 \pm 0.28 \times 10^6$ sites per cell. On the same cells, human lactoferrin binds with a dissociation constant of 1±0.2 μM and $4 \times 10^6 \pm 0.5 \times 10^6$ sites per cell.

This binding to enterocytic cells shows, as in Example 19, that rhLf2 is recognised by the specific lactoferrin receptor in the same way as the native protein is, which suggests good correspondence and a biological activity comparable to that of lactoferrin isolated from milk.

Example 23

Production of Bovine Lactoferrin by Plants and Purification Thereof

Methods such as those described in the invention can also be used for the production of bovine lactoferrin in plants.

References

Alexander B. F. et al, Anim. Genetics, 23, 251-256 (1992).
An et al., Plant Physiol, 81, 301-305 (1986).
An G., Plant Physiol., 81, 86-91 (1986).
Armstrong, Malze Handbook; M. Freeling, V. Walbot Eds.; pp. 665-671 (1994).
Bi B. Y. et al., Eur. J. Cell Biol., 65, 164-171 (1994).
Anderson O. D. et al., Nucleic Acids Research., 17, 431-462 (1989).
Damiens et al., Biochem and Biophys. Acta 14293 (1998)
Depicker et al., J. Mol. Appl. Genet., 1, 561-573 (1982).
Depigny-This et al., Plant. Mol. Biol., 20, 467-479 (1992).
Elass-Rochard E., Roseanu A., Legrand D., Trif M., Salmon V, Motas C., Montreuil J., Spik G., 1995, 312, 839-845.
Elass-Rochard E., Legrand D., Salmon V, Roseanu A., Trif M.,
Tobias P., Mazurier J., Spik G., Infection and Immunity, February, 486-491 (1998).
Franck et al. Cell, 21, 285-294 (1980).
Fillatti J. J. et al. Biotechnologie, 5, 726-730 (1987).
35 Finer J., Plant Cell Report, 11, 323-328 (1992).

Ganiborg O. L. et al. Exp. Cell. Res., 50, 151-158 (1968).
Gaubier et al., Mol. Gen. Genet., 238, 409-418 (1993).
Hanahan D., J. Mol. Biol., 166, 557-580 (1983).
Holsters et al. Mol. Gen. Genet., 163, 181-187 (1978).
Horsch R. B. et al., Science, 227, 1229-1231 (1985). 10 Kay et al., Science, 236, 1299-1302 (1987).
Kamerling et al., Biochem. J. 151, 491-495 (1975).
Klein, Nature, 327, 70-73 (1987).
Laemmli U. K., Nature, 227, 680-685 (1970).
Legrand, D. et al., Biochem. J. 236, 839-844 (1986).
Le Provost F. et al, Biochem. Biophys. Res. Commun., 203, 1324-1332 (1994).
McElroy et al., Mol. Gen. Genet., 231, 150-160 (1991).
Matsuoka K. et Nakamura K., Proc. Natl. Acad. Sci. USA, 88, 834-838 (1991).
Mazurier J. et al., Eur. J. Biochem. 199, 481-487 (1989).
Metz-Boutigue M. H. et al., Eur. J. Biochem. 145, 659-676 (1984).
Mikogami T. et al., J. Am. Physiol. 267, G308-G315 (1994).
Mikogami T. et al., Biochem. J. 308, 391-397 (1995).
Mitra, Plant. Physiol. 106, 977-981 (1994)
Murakami et al., Plant Mol. Biol., 7, 343-355 (1986).
Murashige T. et Skoog F., Physiol. Plantarum, 15, 473-497 (1962).
Ni et al., Plant J., 7, 661-676 (1995).
Pierce et al, Eur. J. Biochem, 1991, 196, 177-184
Powell, M. J. et Ogden, J. E., Nucl. Acids Res. 18, 4013 (1990).
Reina et al., Nucleic Acid Research, 18, 6426 (1990).
Renart J. et Sandoval I. V., Meth. Enzymol., 104, 455-460 (1984).
Rey, M. W. et al., Nucl. Acids Res. 18, 5288 (1990).
Salmon V. et al., Prot. Express. and Purif., 13, 1998, art No. PT980886.
Scatchard, G., Ann. N.Y. Acad. Sci. 51, 660-672 (1949).
Shirsat N. V. et al, Gene, 110, 229-234 (1992).
Spik G. et al., Immunology 35, 663-671 (1978). Spik G. et al., Eur. J. Biochem. 121, 413-419 (1982).
Vain et al., Plant Cell Tissue and organ Culture, 18, 35 143-151 (1989)
Van Berkel, P. H. C. et al., Biochem. J. 319, 117-122 (1996).
Zimecki M. et al., Archiv. Immunol. et Therap. Exper., 1996, 44, 51-56.
Zimecki M. et al., immunol. Lett. 30, 119-124 (1991).

SEQUENCE LISTING

Figure 1:
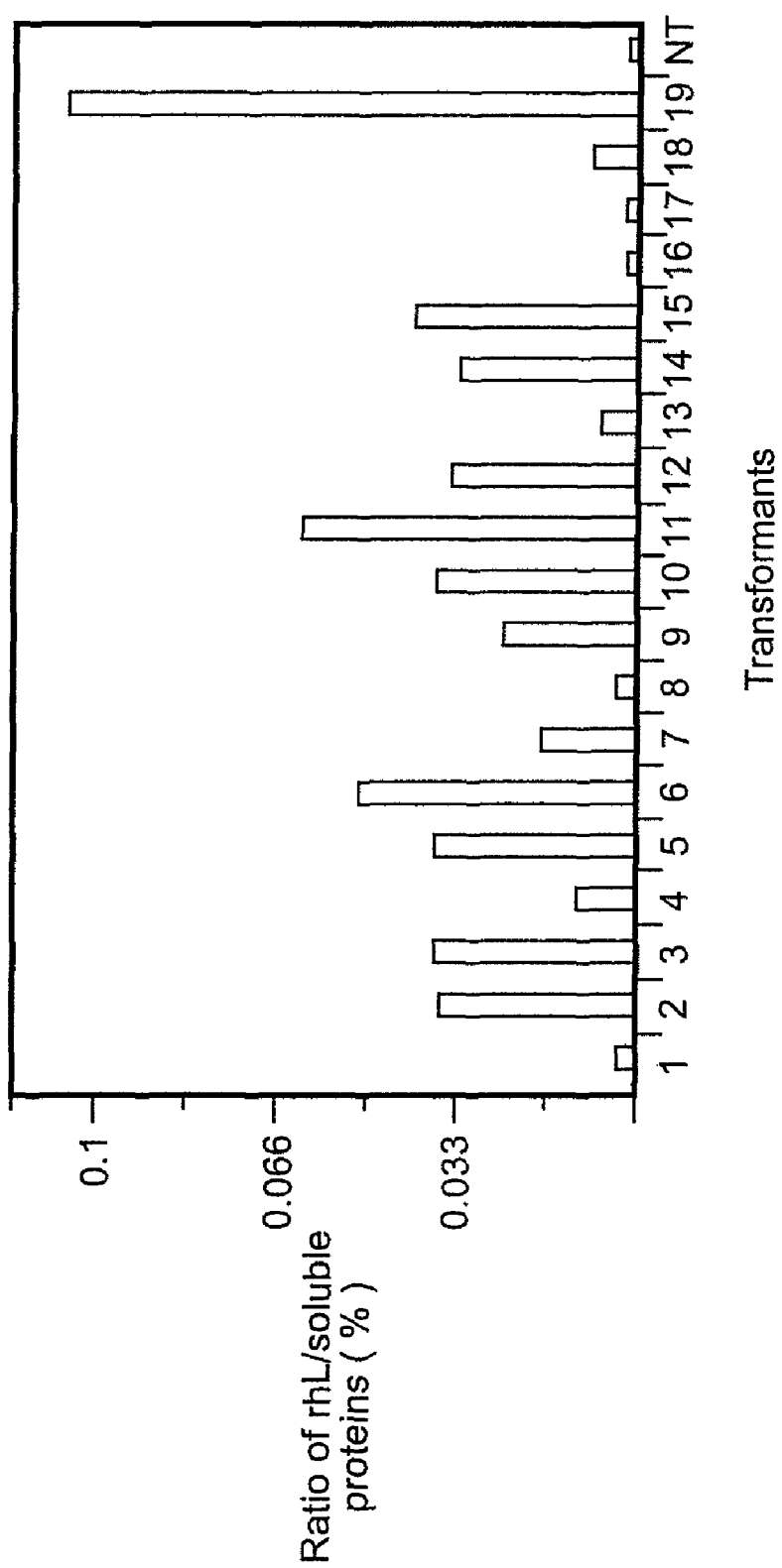
FIG. 1: Rate of expression of rhLf1 as a function of the total quantity of soluble proteins (given as %). Columns 1 to 19: primary transformants. Column NT: non-transformed tobacco.
Figure 2:
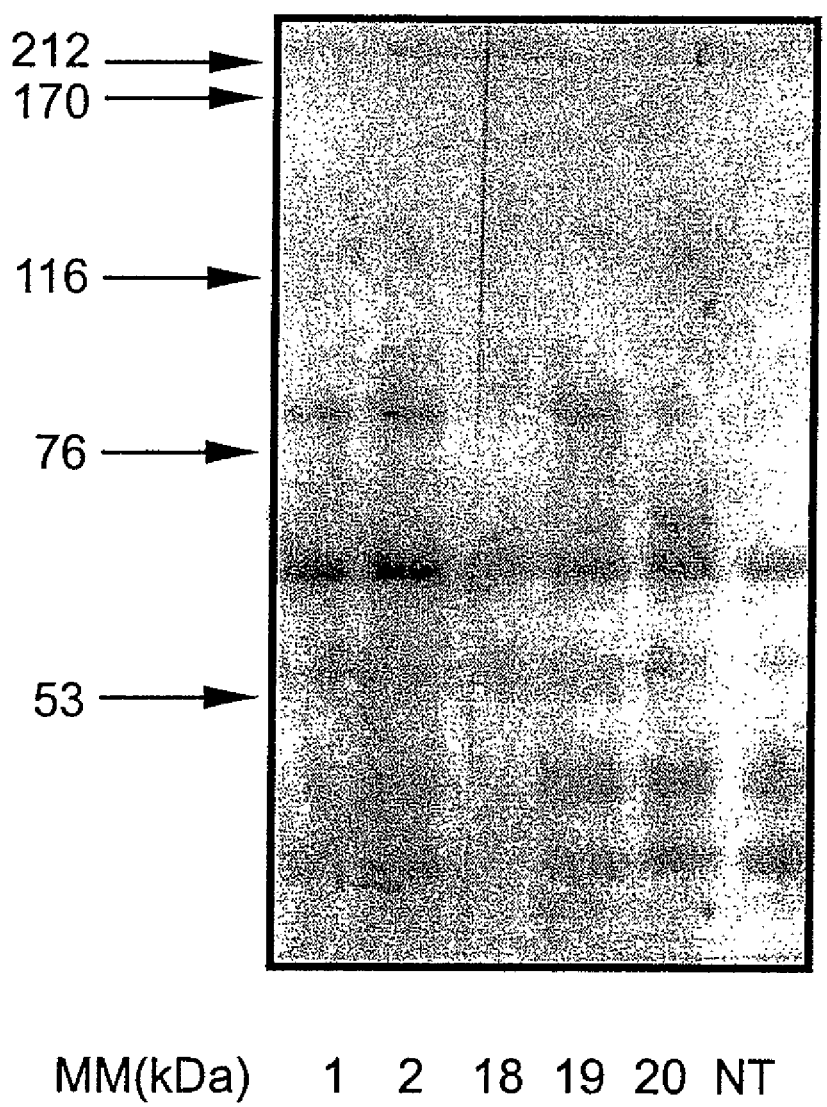
FIG. 2: Detection of rhLf1 by Western Blot method using an extract of the soluble proteins of the primary transformants. Lanes 1, 2, 18, 19, 20: primary transformants. Lane NT: non-transformed tobacco. The positions of the molecular mass controls are shown on the left.
Figure 3:
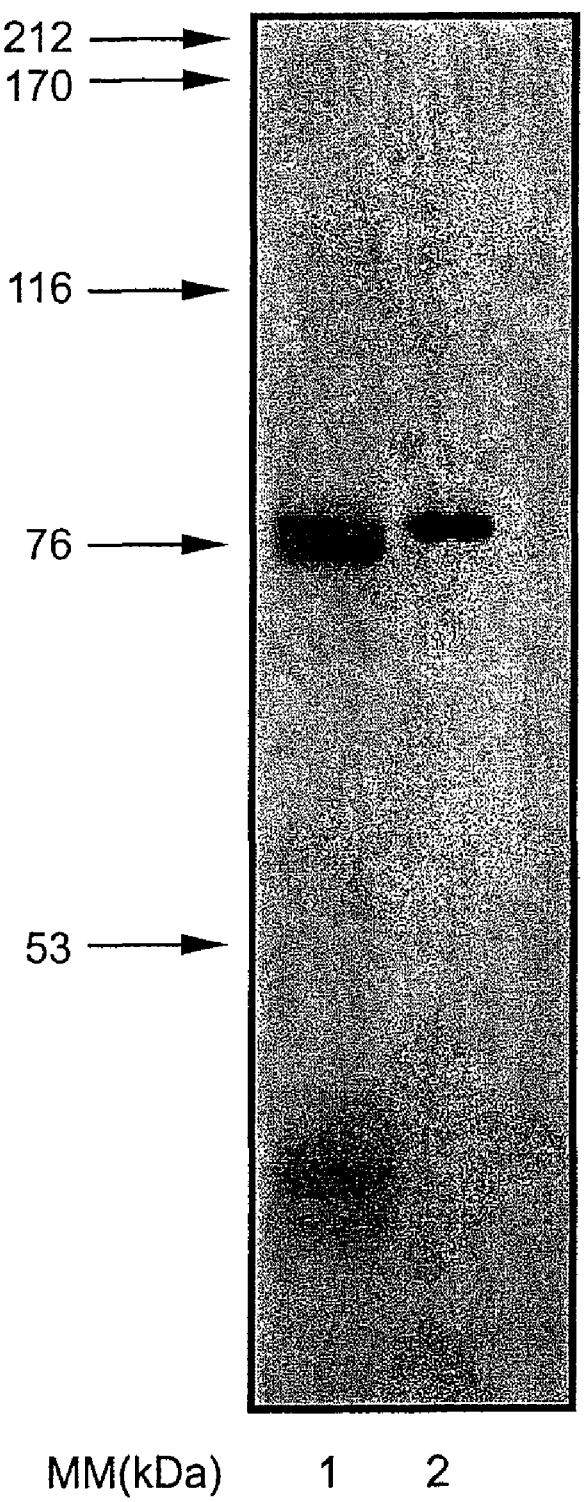
FIG. 3: Detection of rhLf2 by the Western Blot method using a concentrated extract of soluble proteins from transformant T30. Lane (1) analysis of transformant T30. (2) Human Lf, isolated from milk. The positions of the molecular mass controls are shown on the left.
Figure 4:
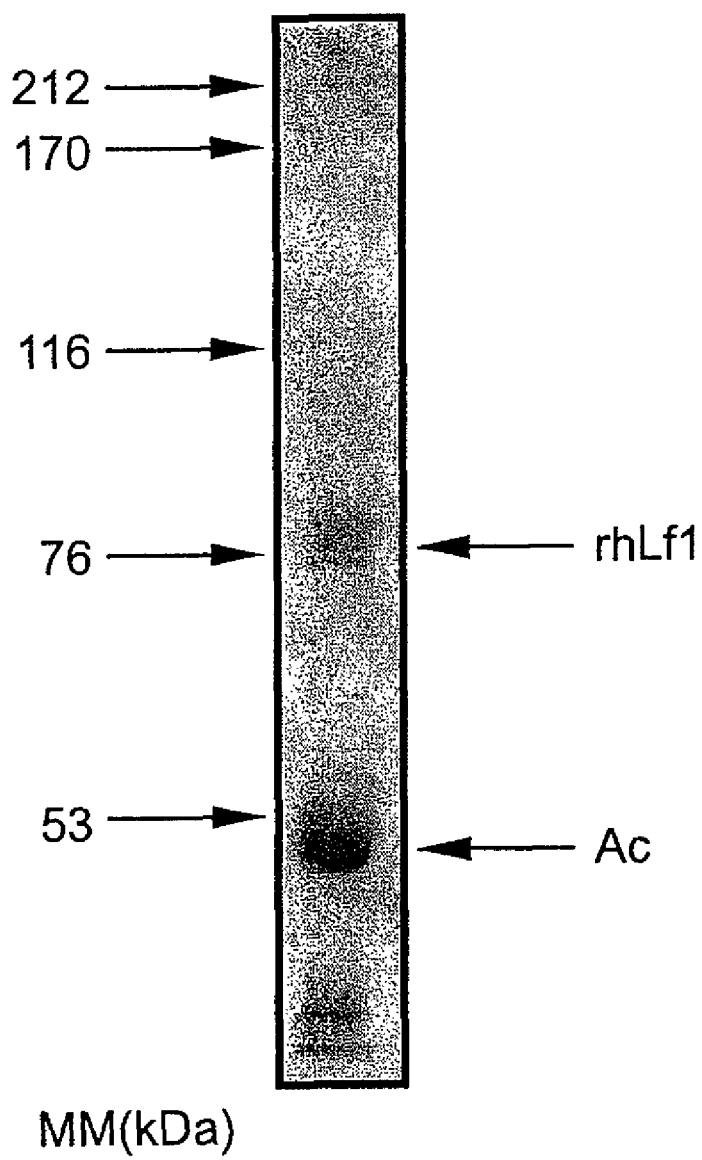
FIG. 4: Detection of rhLf1 by immunoprecipitation using an extract of the soluble proteins of transformant T19. The SDS-PAGE analysis shows the rhLf1 and the anti-Lf antibodies (Ab). The positions of the molecular mass controls are shown on the left.
Figure 5:
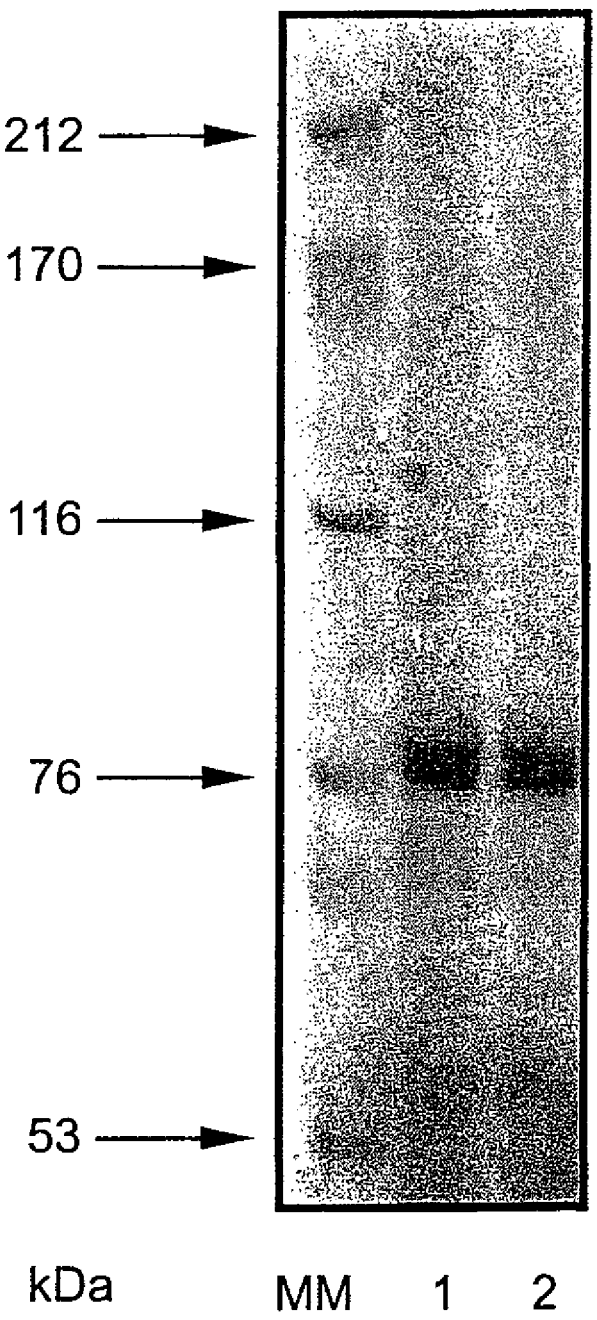
FIG. 5: Analysis of rhLf1 and rhLf2 after purification by means of affinity chromatography.
Lane (1): rhLf1; lane (2): rhLf2. The positions of the molecular mass controls are shown on the left.
Figure 6:
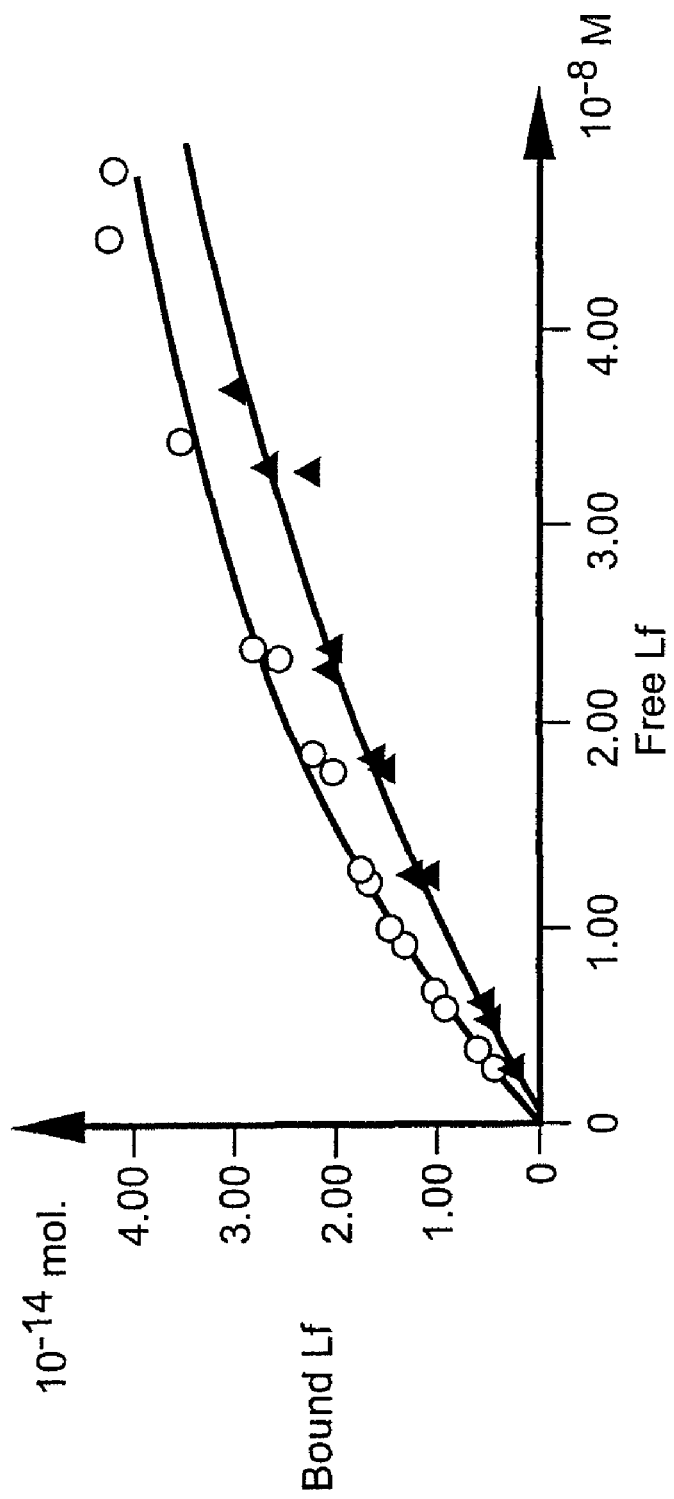
FIG. 6: Specific binding of rhLf2 (▲) and milk hLf (○) on Jurkat lymphoblastic cells. The lactoferrins are labelled with $^{125}$I. Non-specific binding is measured in 100 molar excess of non-labelled native Lf, and represents approximately 25% of total binding. These values were determined by two separate experiments, both of which were carried out twice.
Figure 7:
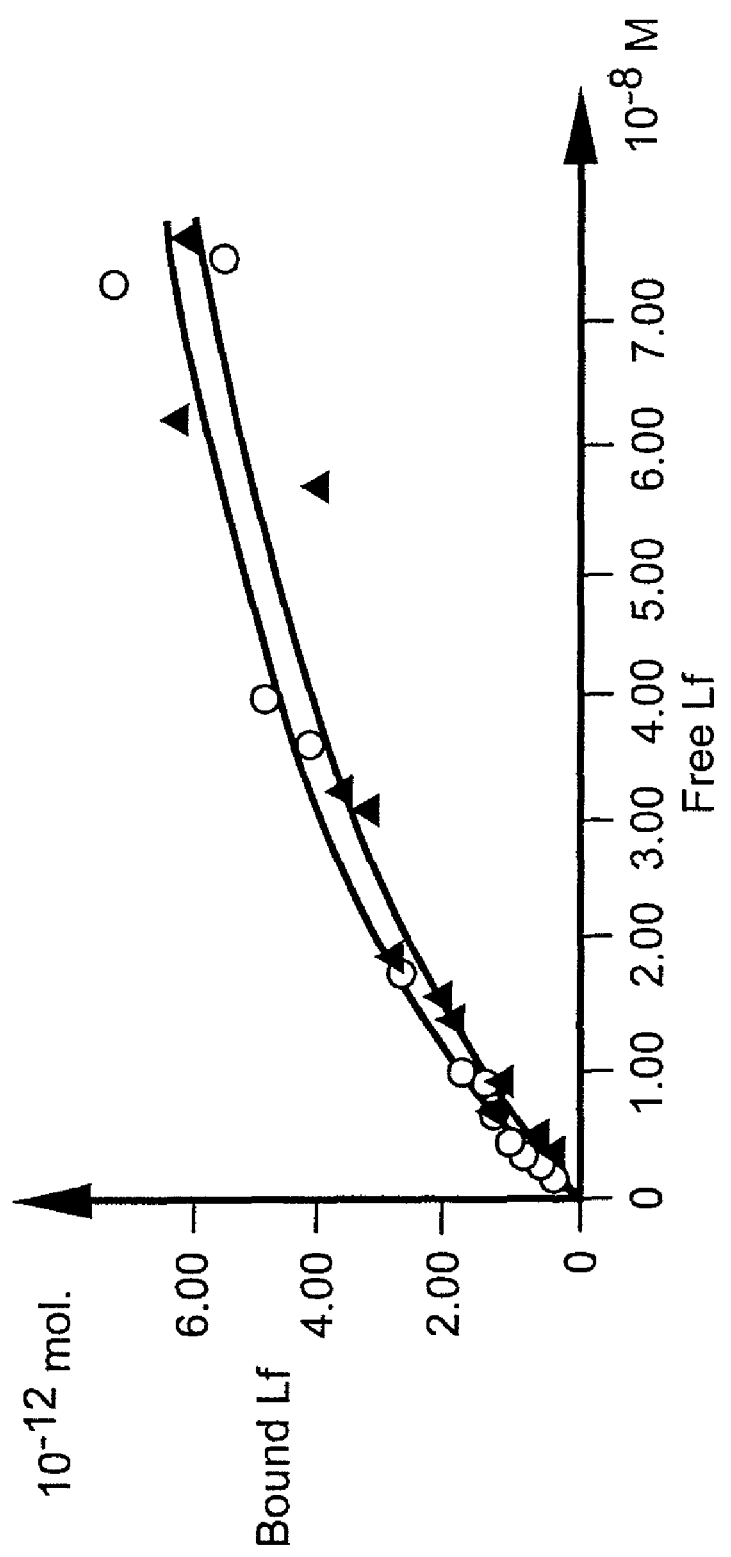
FIG. 7: Specific binding of rhLf2 (▲) and milk hLf (○) on HT29 enterocytic cells. The lactoferrins are labelled with $^{125}$I. Non-specific binding is measured in the presence of 100 molar excess of non-labelled native Lf, and represents approximately 25% of total binding. These values were determined by two separate experiments, each of which was carried out twice.

```
<160> NUMBER OF SEQ ID NOS: 13

<210> SEQ ID NO 1
<211> LENGTH: 4
<212> TYPE: PRT
<213> ORGANISM: Unknown
<220> FEATURE:
<223> OTHER INFORMATION: Protein localization sequence

<400> SEQUENCE: 1

Lys Asp Glu Leu
1

<210> SEQ ID NO 2
<211> LENGTH: 6
<212> TYPE: PRT
<213> ORGANISM: Unknown
<220> FEATURE:
<223> OTHER INFORMATION: Protein localization sequence
```

-continued

```
<400> SEQUENCE: 2

Ser Glu Lys Asp Glu Leu
1               5

<210> SEQ ID NO 3
<211> LENGTH: 4
<212> TYPE: PRT
<213> ORGANISM: Unknown
<220> FEATURE:
<223> OTHER INFORMATION: Protein localization sequence

<400> SEQUENCE: 3

His Asp Glu Leu
1

<210> SEQ ID NO 4
<211> LENGTH: 19
<212> TYPE: PRT
<213> ORGANISM: Unknown
<220> FEATURE:
<223> OTHER INFORMATION: Protein localization sequence

<400> SEQUENCE: 4

Met Lys Leu Val Phe Leu Val Leu Leu Phe Leu Gly Ala Leu Gly Leu
1               5                   10                  15

Cys Leu Ala

<210> SEQ ID NO 5
<211> LENGTH: 23
<212> TYPE: DNA
<213> ORGANISM: Artificial Sequence
<220> FEATURE:
<223> OTHER INFORMATION: Synthetic sequence

<400> SEQUENCE: 5
atgacaacac tgagtgtctg gcc                                          23

<210> SEQ ID NO 6
<211> LENGTH: 38
<212> TYPE: DNA
<213> ORGANISM: Artificial Sequence
<220> FEATURE:
<223> OTHER INFORMATION: Synthetic sequence

<400> SEQUENCE: 6
ccgtctagag aattcgtttt acttcctgag gagttcac                           38

<210> SEQ ID NO 7
<211> LENGTH: 23
<212> TYPE: PRT
<213> ORGANISM: Sweet potato sporamin

<400> SEQUENCE: 7

Met Lys Ala Phe Thr Leu Ala Leu Phe Leu Ala Leu Ser Leu Tyr Leu
1               5                   10                  15

Leu Pro Asn Pro Ala His Ser
            20

<210> SEQ ID NO 8
<211> LENGTH: 39
<212> TYPE: DNA
<213> ORGANISM: Artificial Sequence
<220> FEATURE:
<223> OTHER INFORMATION: Synthetic sequence
```

```
<400> SEQUENCE: 8
taactcgagg ccgggtcgac ggagaaggag tgttcagtg                    39

<210> SEQ ID NO 9
<211> LENGTH: 27
<212> TYPE: DNA
<213> ORGANISM: Artificial Sequence
<220> FEATURE:
<223> OTHER INFORMATION: Syntthetic sequence

<400> SEQUENCE: 9
acccgtccaa ttcaagaatg gacgaag                                 27

<210> SEQ ID NO 10
<211> LENGTH: 15
<212> TYPE: DNA
<213> ORGANISM: Artificial Sequence
<220> FEATURE:
<223> OTHER INFORMATION: Syntthetic sequence

<400> SEQUENCE: 10
ccaattcaag aatgg                                              15

<210> SEQ ID NO 11
<211> LENGTH: 33
<212> TYPE: DNA
<213> ORGANISM: Artificial Sequence
<220> FEATURE:
<223> OTHER INFORMATION: Syntthetic sequence

<400> SEQUENCE: 11
tccctcgagg aattcatgaa agccttcaca ctc                          33

<210> SEQ ID NO 12
<211> LENGTH: 32
<212> TYPE: DNA
<213> ORGANISM: Artificial Sequence
<220> FEATURE:
<223> OTHER INFORMATION: Syntthetic sequence

<400> SEQUENCE: 12
tccgtcgacc ggaatgggct ggattgggca gg                           32

<210> SEQ ID NO 13
<211> LENGTH: 7
<212> TYPE: PRT
<213> ORGANISM: Homo sapiens

<400> SEQUENCE: 13

Gly Arg Arg Arg Arg Ser Val
1               5
```

The invention claimed is:

1. A pharmaceutical composition comprising mature lactoferrin obtained by a method of producing lactoferrin comprising: transforming plant cells using a vector comprising a nucleotide sequence which comprises: (i) a coding sequence for the mature lactoferrin protein and (ii) elements required by a plant cell to produce the lactoferrin coded by the sequence so as to integrate the recombinant sequence within the genome of the cells; and recovering recombinant mature lactoferrin protein produced in the transformed cells, wherein the plant cells are from a monocotyledonous plant or a dicotyledonous plant.

2. The pharmaceutical composition of claim 1, wherein recovering recombinant mature lactoferrin comprises extracting the lactoferrin from the cells followed by purifying the lactoferrin.

3. A pharmaceutical composition comprising mature lactoferrin obtained by a method of producing mature lactoferrin comprising: (a) transforming plant cells so as to integrate a recombinant nucleotide sequence within the genome of the plant cells, the recombinant nucleotide sequence comprising: (i) a coding sequence for the mature lactoferrin, (ii) a transcription promoter and terminator which are operatively linked to the coding sequence of (i) and are recognized by transcriptional machinery of plant cells, and (iii) a coding sequence for a signal peptide that directs secretions of recombinant peptides from plant cells (b) expressing lactoferrin in said transformed plant cells, and (c) recovering the lactoferrin expressed in said transformed plant cells, wherein the expressed lactoferrin is mature lactoferrin, wherein the plant cells are from a monocotyledonous plant or a dicotyledonous plant.

4. The pharmaceutical composition of claim 3, wherein the coding sequence for the lactoferrin is a coding sequence for human lactoferrin.

5. The pharmaceutical composition of claim 3, wherein the coding sequence for a signal peptide is a sequence selected from the group consisting of a coding sequence for a signal peptide of lactoferrin, a coding sequence for the signal peptide of sweet potato sporamin A and a coding sequence for PRS (pathogenesis related protein).

6. The pharmaceutical composition of claim 3, wherein the terminator is selected from the group consisting of the terminator polyA 35S of the CaMV (cauliflower mosaic virus), and the terminator polyA NOS of Agrobacterium tumefaciens and is located downstream of the coding sequence for the mature lactoferrin.

7. The pharmaceutical composition of claim 3, wherein the transcription promoter is selected from the group consisting of the 35S promoter of the CaMV, the double constitutive promoter of the CaMV, the promoter pCRU of the radish cruciferin gene, the promoters pGA1 and pGA6 of Arabidopsis thaliana, the chimeric promoter super-promoter PSP of Agrobacterium tumefaciens, the rice actin promoter followed by the actin intron PAR-IRA promoter, the wheat HMWG promoter, and the maize gamma-zein promoter.

8. The pharmaceutical composition of claim 3, wherein the recovering of the recombinant lactoferrin is by extraction followed by purification.

9. The pharmaceutical composition of claim 3, wherein the transforming of plant cells is by means of Agrobacterium tumefaciens transformed by a vector containing the recombinant sequence.

10. The pharmaceutical composition of claim 3, wherein: the coding sequence for lactoferrin is a coding sequence for human lactoferrin, the coding sequence for a signal peptide is a coding sequence for a signal peptide of sweet potato sporamin A, the terminator is the terminator polyA 35S of the CaMV, and the transcription promoter is the wheat HMWG promoter.

11. A pharmaceutical composition comprising lactoferrin obtained by the method of producing mature lactoferrin comprising: (a) transforming plant cells so as to integrate a recombinant nucleotide sequence within the genome of the plant cells and the recombinant nucleotide sequence comprising: (i) the coding sequence for the mature lactoferrin, (ii) a transcription promoter and terminator which are operably linked to the coding sequence of (i) and are recognized by transcriptional machinery of plant cells, and (iii) a coding sequence for a signal peptide that directs secretion of recombinate peptides from plant cells; (b) producing transformed plants from the transformed plant cells; (c) expressing lactoferrin from said transformed plants, and (d) recovering the lactoferrin expressed from said transformed plants, wherein the expressed lactoferrin is mature lactoferrin, wherein the plant cells are from a monocotyledonous plant or a dicotyledonous plant.

12. The pharmaceutical composition of claim 11, wherein the coding sequence for the mature lactoferrin is a coding sequence for human lactoferrin.

13. The pharmaceutical composition of claim 11, wherein the coding sequence for the signal peptide is a sequence selected from the group consisting of a coding sequence for a signal peptide of lactoferrin, a coding sequence for the signal peptide of sweet potato sporamin A and a coding sequence for PRS.

14. The pharmaceutical composition of claim 11, wherein the terminator is selected from the group consisting of the terminator polyA 35S of the CaMV, and the terminator polyA NOS of Agrobacterium tumefaciens and is located downstream of the coding sequence for the mature lactoferrin.

15. The pharmaceutical composition of claim 11, wherein the transcription promoter is selected from the group consisting of the 35S promoter of the CaMV, the double constitutive promoter of the CaMV, the promoter pCRU of the radish cruciferin gene, the promoters pGA1 and pGA6 of Arabidopsis thaliana, the chimeric promoter super-promoter PSP of Agrobacterium tumefaciens, the rice actin promoter followed by the actin intron PAR-IRA promoter, the wheat HMWG promoter, and the maize gamma-zein promoter.

16. The pharmaceutical composition of claim 11, wherein the recovering of the recombinant mature lactoferrin is by extraction followed by purification.

17. The pharmaceutical composition of claim 11, wherein the transforming of plant cells is by means of Agrobacterium tumefaciens transformed by a vector containing the recombinant sequence.

18. The pharmaceutical composition of claim 11, wherein: the coding sequence for lactoferrin is a coding sequence for human lactoferrin, the coding sequence for a signal peptide is a coding sequence for a signal peptide of sweet potato sporamin A, the terminator is the terminator polyA 35S of the CaMV, and the transcription promoter is the wheat HMWG promoter.

19. A pharmaceutical composition comprising mature lactoferrin obtained by a method of producing lactoferrin comprising: transforming plant cells using a vector comprising a nucleotide sequence which comprises: (i) a coding sequence for the mature lactoferrin protein and (ii) elements required by a plant cell to produce the lactoferrin coded by the sequence so as to integrate the recombinant sequence within the genome of the cell; producing transformed plants from the transformed cells; and recovering recombinant mature lactoferrin protein produced in the transformed plants, wherein the plant cells are from a monocotyledonous plant or a dicotyledonous plant .

20. The pharmaceutical composition of claim 19, wherein recovering recombinant mature lactoferrin comprises extracting the lactoferrin from the plants followed by purifying the lactoferrin.

* * * * *